(12) United States Patent
Weichert et al.

(10) Patent No.: US 6,573,288 B1
(45) Date of Patent: Jun. 3, 2003

(54) SUBSTITUTED SULPHONYL CYANAMIDES, METHOD FOR PRODUCING SAME AND THEIR USE AS MEDICAMENT

(75) Inventors: Andreas Weichert, Egelsbach (DE); Hans Jochen Lang, Hofheim (DE); Stefan Petry, Frankfurt (DE); Jan-Robert Schwark, Kelkheim (DE); Heinz-Werner Kleemann, Bischofsheim (DE); Sabine Faber, Idstein (DE); Hans-Willi Jansen, Niedernhausen (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 09/674,606

(22) PCT Filed: Apr. 30, 1999

(86) PCT No.: PCT/EP99/02940

§ 371 (c)(1),
(2), (4) Date: Nov. 3, 2000

(87) PCT Pub. No.: WO99/57102

PCT Pub. Date: Nov. 11, 1999

(30) Foreign Application Priority Data

May 6, 1998 (DE) .......................................... 198 20 064

(51) Int. Cl.[7] ..................... C07D 233/90; A61K 31/415
(52) U.S. Cl. .................... 514/398; 514/399; 548/322.5; 548/325.1; 548/327.1; 548/333.1
(58) Field of Search ........................ 548/327.1, 322.5, 548/325.1, 331.1; 514/386, 398

(56) References Cited

U.S. PATENT DOCUMENTS

| | | | | |
|---|---|---|---|---|
| 5,310,929 A | * | 5/1994 | Ardeccky et al. ............ 548/253 |
| 5,391,732 A | * | 2/1995 | Bhatnagar et al. .......... 540/603 |
| 5,708,034 A | * | 1/1998 | Kleeman et al. ............. 514/618 |
| 6,335,451 B1 | | 1/2002 | Kleeman et al. ............. 514/398 |
| 6,369,069 B1 | | 4/2002 | Kleemann et al. .......... 514/277 |

FOREIGN PATENT DOCUMENTS

WO  WO 99/40064  8/1999

* cited by examiner

Primary Examiner—Joseph K. McKane
Assistant Examiner—Kamal Saeed
(74) Attorney, Agent, or Firm—Finnegan, Henderson, Farabow, Garrett & Dunner, LLP

(57) ABSTRACT

The invention relates to compounds of formula (I) in which the symbols have the meanings given in the claims. Said compounds are inhibitors of the sodium-dependent bicarbonate/chloride ion exchanger which can be used as medicines for the prophylaxis or treatment of a wide range of diseases, for example the treatment and/or prophylaxis of myocardial infarction, angina pectoris, diseases caused by ischaemia, impaired respiration, cardiac ischaemia, ischaemia of the peripheral and central nervous system and stroke, ischaemia of the peripheral organs and limbs and diseases in which cell proliferation is a primary or secondary cause, in the treatment of shock, during surgical interventions and organ transplants or for preserving and storing transplants to be used in surgical interventions.

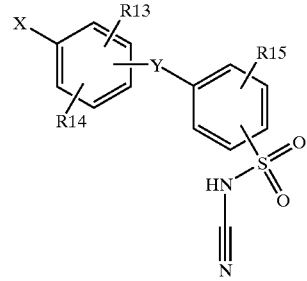

(I)

30 Claims, No Drawings

SUBSTITUTED SULPHONYL CYANAMIDES, METHOD FOR PRODUCING SAME AND THEIR USE AS MEDICAMENT

This application is a 371 of PCT/EP99/02940 filed Apr. 30, 1999.

The present invention relates to compounds of the formula (I)

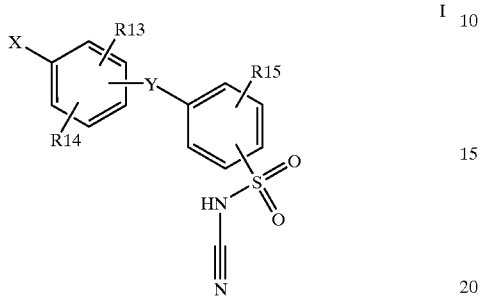

in which the symbols have the following meanings:
X is equal to

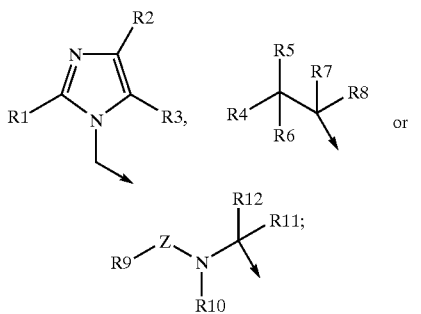

R(1) is hydrogen, alkyl having 1, 2, 3, 4, 5, 6, 7 or 8 carbon atoms; or —$C_aH_{2a}$-phenyl,
where the phenyl moiety is unsubstituted or substituted by 1, 2 or 3 identical or different radicals from the group F, Cl, Br, I, $CF_3$, methyl, methoxy, hydroxy or NR(19)R(20);
R(19) and R(20) independently of one another are H or alkyl having 1, 2, 3 or 4 carbon atoms;
a is zero, 1 or 2; or
R(1) is —$C_bH_{2b}$-heteroaryl having 1, 2, 3, 4, 5, 6, 7, 8 or 9 carbon atoms where the heteroaryl moiety is unsubstituted or substituted by 1, 2 or 3 identical or different radicals from the series consisting of F, Cl, Br, I, $CF_3$, $CH_3$, methoxy, hydroxy or NR(21)R(22);
R(21) and R(22) independently of one another are H or alkyl having 1, 2, 3 or 4 carbon atoms;
b is zero, 1 or 2; or
R(1) is —$C_cH_{2c}$-cycloalkyl having 3, 4, 5, 6 or 7 carbon atoms;
c is zero, 1 or 2;
R(2) and R(3) independently of one another are hydrogen, F, Cl, Br, I, $CF_3$, —CN, —$NO_2$, $CH_2OR(23)$, CO—R(24) or O—R(25);
R(23) is hydrogen or alkyl having 1, 2, 3, 4, 5, 6, 7 or 8 carbon atoms;
R(24) is hydrogen, alkyl having 1, 2, 3, 4, 5, 6, 7 or 8 carbon atoms, OR(26) or phenyl;
where phenyl is unsubstituted or substituted by 1, 2 or 3 identical or different radicals from the series consisting of F, Cl, Br, I, $CF_3$, methyl, methoxy, hydroxy or NR(27)R(28);
R(27) and R(28) independently of one another are H or alkyl having 1, 2, 3 or 4 carbon atoms;
R(26) is hydrogen or alkyl having 1, 2, 3, 4, 5, 6, 7 or 8 carbon atoms;
R(25) is hydrogen, alkyl having 1, 2, 3, 4, 5, 6, 7 or 8 carbon atoms, or phenyl;
where phenyl is unsubstituted or substituted by 1, 2 or 3 identical or different radicals from the series consisting of F, Cl, Br, I, $CF_3$, methyl, methoxy, hydroxy or NR(29)R(30);
R(29) and R(30) independently of one another are H or alkyl having 1, 2, 3 or 4 carbon atoms; or
R(25) is heteroaryl having 1, 2, 3, 4, 5, 6, 7, 8 or 9 carbon atoms, which is unsubstituted or substituted by 1, 2 or 3 identical or different radicals from the series consisting of F, Cl, Br, I, $CF_3$, $CH_3$, methoxy, hydroxy or NR(31)R(32);
R(31) and R(32) independently of one another are H or alkyl having 1, 2, 3 or 4 carbon atoms; or
R(2) and R(3) independently of one another are alkyl having 1, 2, 3, 4, 5, 6, 7 or 8 carbon atoms, cycloalkyl having 3, 4, 5, 6 or 7 carbon atoms; or
—$C_dH_{2d}$-phenyl, where the phenyl moiety is unsubstituted or substituted by 1, 2 or 3 identical or different radicals from the series consisting of F, Cl, Br, I, $CF_3$, methyl, methoxy, hydroxy or NR(33)R(34);
R(33) and R(34) independently of one another are H or alkyl having 1, 2, 3 or 4 carbon atoms;
d is zero, 1 or 2; or
R(2) and R(3) independently of one another are
—$C_eH_{2e}$-heteroaryl having 1, 2, 3, 4, 5, 6, 7, 8 or 9 carbon atoms, where the heteroaryl moiety is unsubstituted or substituted by 1, 2 or 3 identical or different radicals from the series consisting of F, Cl, Br, I, $CF_3$, $CH_3$, methoxy, hydroxy or NR(35)R(36);
R(35) and R(36) independently of one another are H or alkyl having 1, 2, 3 or 4 carbon atoms;
e is zero, 1 or 2; or
R(2) and R(3) independently of one another are
—$SO_f$—R(37);
R(37) is alkyl having 1, 2, 3, 4, 5, 6, 7 or 8 carbon atoms, cycloalkyl having 3, 4, 5, 6 or 7 carbon atoms, or —$C_gH_{2g}$-phenyl, where the phenyl moiety is unsubstituted or substituted by 1, 2 or 3 identical or different radicals from the series consisting of F, Cl, Br, I, $CF_3$, methyl, methoxy, hydroxy or NR(38)R(39);
R(38) and R(39) independently of one another are H or alkyl having 1, 2, 3 or 4 carbon atoms;
f is zero, 1 or 2;
g is zero, 1 or 2;
R(4) is hydrogen, alkyl having 1, 2, 3, 4, 5, 6, 7 or 8 carbon atoms, 1-naphthyl, 2-naphthyl, —$C_iH_{2i}$-cycloalkyl having 3, 4, 5, 6 or 7 carbon atoms or —$C_iH_{2i}$-phenyl, where the phenyl moiety is unsubstituted or substituted by 1, 2 or 3 identical or different radicals from the series consisting of alkyl having 1, 2, 3, 4, 5, 6, 7 or 8 carbon atoms, F, Cl, Br, I, $CF_3$, $SO_jR(48)$, OR(49), NR(50)R(51), —CN, —$NO_2$ or CO—R(52);
i is zero, 1 or 2;
R(48) is alkyl having 1, 2, 3 or 4 carbon atoms or NR(53)R(54);
R(53) and R(54) independently of one another are hydrogen or alkyl having 1, 2, 3 or 4 carbon atoms;

j is zero, 1 or 2;
R(49) is hydrogen or alkyl having 1, 2, 3 or 4 carbon atoms;
R(50) and R(51) independently of one another are hydrogen or alkyl having 1, 2, 3 or 4 carbon atoms;
R(52) is hydrogen, alkyl having 1, 2, 3, 4, 5, 6, 7 or 8 carbon atoms or OR(55);
R(55) is hydrogen, alkyl having 1, 2, 3, 4, 5, 6, 7, or 8 carbon atoms; or R(4) and R(6) together with the carbon atom carrying them are cycloalkyl having 3, 4, 5, 6 or 7 carbon atoms or fluorenyl;

R(5), R(6), R(7) and R(8) independently of one another are hydrogen, F, $CF_3$, O—R(56), alkyl having 1, 2, 3, 4, 5, 6, 7 or 8 carbon atoms, cycloalkyl having 3, 4, 5, 6 or 7 carbon atoms, —$C_kH_{2k}$-phenyl, where the phenyl moiety is unsubstituted or substituted by 1, 2 or 3 identical or different radicals from the series consisting of F, Cl, Br, I, $CF_3$, methyl, methoxy, hydroxy or NR(57)R(58);
R(57) and R(58) independently of one another are hydrogen or alkyl having 1, 2, 3 or 4 carbon atoms;
k is zero, 1 or 2;
R(56) is hydrogen, alkyl having 1, 2, 3, 4, 5, 6, 7 or 8 carbon atoms, or phenyl, which is unsubstituted or substituted by 1, 2 or 3 identical or different radicals from the series consisting of F, Cl, Br, I, $CF_3$, methyl, methoxy, hydroxy or NR(59)R(60);
R(59) and R(60) independently of one another are hydrogen or alkyl having 1, 2, 3 or 4 carbon atoms, or
R(56) is heteroaryl having 1, 2, 3, 4, 5, 6, 7, 8 or 9 carbon atoms, which is unsubstituted or substituted by 1, 2 or 3 identical or different radicals from the series consisting of F, Cl, Br, I, $CF_3$, $CH_3$, methoxy, hydroxy or NR(61)R(62);
R(61) and R(62) independently of one another are hydrogen or alkyl having 1, 2, 3 or 4 carbon atoms; or
R(5) and R(7) together are a second bond between the carbon atoms carrying the radicals R(6) and R(8), where R(4), R(6) and R(8) are as defined above;
R(9) is alkyl having 1, 2, 3, 4, 5, 6, 7 or 8 carbon atoms, alkenyl having 2, 3, 4, 5, 6, 7 or 8 carbon atoms, or —$C_IH_{2I-II}$—A;
II is zero or 2; and
I is zero, 1, 2, 3 or 4;
where I is unequal to zero or 1, when II is equal to 2;
R(10) is hydrogen;
alkyl having 1, 2, 3, 4, 5, 6, 7 or 8 carbon atoms; or
alkenyl having 2, 3, 4, 5, 6, 7 or 8 carbon atoms;

—$C_mH_{2m-mm}$—B,
mm is zero or 2; and
m is zero, 1, 2, 3 or 4;
where m is unequal to zero or 1, when mm is equal to 2;
R(11) and R(12) independently of one another are hydrogen or alkyl having 1, 2, 3, 4, 5, 6, 7 or 8 carbon atoms;
Z is carbonyl or sulfonyl;
A and B independently of one another are
1. aryl having 6, 7, 8, 9, 10, 11, 12, 13 or 14 carbon atoms, preferably phenyl, 1-naphthyl or 2-naphthyl;
2. a radical as defined in 1, substituted by 1, 2 or 3 identical or different radicals from the series consisting of alkyl having 1, 2, 3, 4, 5, 6, 7 or 8 carbon atoms, F, Cl, Br, I, $CF_3$, $SO_nR(63)$, OR(64), NR(65)R(66), —CN, —$NO_2$ or CO—R(67);
3. heteroaryl having 1, 2, 3, 4, 5, 6, 7, 8 or 9 carbon atoms;
4. a radical as defined in 3, substituted by 1, 2 or 3 identical or different radicals from the series consisting of F, Cl, Br, I, $CF_3$, $CH_3$, methoxy, hydroxy or NR(68)R(69);
5. cycloalkyl having 3, 4, 5, 6 or 7 carbon atoms;
6. O—R(70); or
7. O—R(71);
n is zero, 1 or 2;
R(70) and R(71) independently of one another are
1. hydrogen;
2. alkyl having 1, 2, 3, 4, 5, 6, 7 or 8 carbon atoms;
3. —$C_oH_{2o-oo}$-phenyl,
oo is zero or 2; and
o is zero, 1, 2, 3 or 4;
where o is unequal to zero or 1, when oo is equal to 2;
4. a radical as defined in 3, where the phenyl moiety is substituted by 1, 2 or 3 identical or different radicals from the series consisting of alkyl having 1, 2, 3, 4, 5, 6, 7 or 8 carbon atoms, F, Cl, Br, I, $CF_3$, $SO_pR(72)$, OR(73), NR(74)R(75), —CN, —$NO_2$ or CO—R(76); or
5. alkenyl having 2, 3, 4, 5, 6, 7 or 8 carbon atoms;
R(63) and R(72) independently of one another are alkyl having 1, 2, 3 or 4 carbon atoms or NR(77)R(78);
R(67) and R(76) independently of one another are hydrogen, alkyl having 1, 2, 3, 4, 5, 6, 7 or 8 carbon atoms or OR(89);
R(89) is hydrogen or alkyl having 1, 2, 3, 4, 5, 6, 7 or, 8 carbon atoms;
R(64), R(65), R(66), R(68), R(69), R(73), R(74), R(75), R(77) and R(78) independently of one another are hydrogen or alkyl having 1, 2, 3 or 4 carbon atoms;
p is 1 or 2;
R(13), R(14) and R(15) independently of one another are hydrogen, alkyl having 1, 2, 3, 4, 5, 6, 7 or 8 carbon atoms, F, Cl, Br, I, $CF_3$, —CN, —$NO_2$, $SO_q$—R(79), CO—R(80) or O—R(81);
q is zero, 1, or 2;
R(79) is alkyl having 1, 2, 3, 4, 5, 6, 7 or 8 carbon atoms or phenyl, which is unsubstituted or substituted by 1, 2 or 3 identical or different radicals from the series consisting of F, Cl, Br, I, CF3, methyl, methoxy, hydroxy or NR(82)R(83);
R(82), R(83) independently of one another are hydrogen or alkyl having 1, 2, 3 or 4 carbon atoms;
R(80) is hydrogen, alkyl having 1, 2, 3, 4, 5, 6, 7 or 8 carbon atoms or OR(84);
R(84) is hydrogen or alkyl having 1, 2, 3, 4, 5, 6, 7 or 8 carbon atoms;
R(81) is hydrogen, alkyl having 1, 2, 3, 4, 5, 6, 7 or 8 carbon atoms or phenyl, which is unsubstituted or substituted by 1, 2 or 3 identical or different radicals from the series consisting of F, Cl, Br, I, CF3, methyl, methoxy, hydroxy or NR(82)R(83);
Y is CR(16)R(17), CO, S, $SO_2$, O, NR(18),
R(16) is hydrogen or —OR(85);
R(85) is hydrogen, alkyl having 1, 2, 3, 4, 5, 6, 7 or 8 carbon atoms or CO—R(86);
R(86) is alkyl having 1, 2, 3, 4, 5, 6, 7 or 8 carbon atoms or phenyl, which is unsubstituted or substituted by 1, 2 or 3 identical or different radicals from the series consisting of F, Cl, Br, I, $CF_3$, methyl, methoxy or hydroxyl;

R(17) is hydrogen or alkyl having 1, 2, 3, 4, 5, 6, 7 or 8 carbon atoms;

R(18) is hydrogen, alkyl having 1, 2, 3, 4, 5, 6, 7 or 8 carbon atoms, CO—R(87) or $SO_2R(88)$;

R(87) and R(88) independently of one another are alkyl having 1, 2, 3, 4, 5, 6, 7 or 8 carbon atoms, cycloalkyl having 3, 4, 5, 6, 7 or 8 carbon atoms or phenyl, which is unsubstituted or substituted by 1, 2 or 3 identical or different radicals from the series consisting of F, Cl, Br, I, $CF_3$, methyl, methoxy or hydroxyl;

and their physiologically tolerable salts.

Preferred compounds of the formula (I) are those in which:

X is equal to

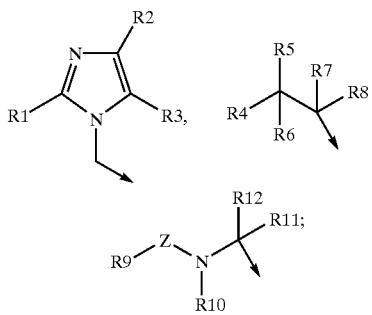

R(1) is hydrogen, alkyl having 1, 2, 3 or 4 carbon atoms or —$C_aH_{2a}$-phenyl, where the phenyl moiety is unsubstituted or substituted by 1, 2 or 3 identical or different radicals from the series consisting of F, Cl, Br, I, $CF_3$, methyl, methoxy or hydroxyl;

a is zero or 1; or

R(1) is heteroaryl having 1, 2, 3, 4, 5, 6, 7, 8 or 9 carbon atoms, which is unsubstituted or substituted by 1, 2 or 3 identical or different radicals from the series consisting of F, Cl, Br, I, $CF_3$, $CH_3$, methoxy or hydroxyl; or R(1) is —$C_cH_{2c}$-cycloalkyl having 3, 4, 5, 6 or 7 carbon atoms; c is zero or 1;

R(2) and R(3) independently of one another are hydrogen, F, Cl, Br, I, $CF_3$, —CN, —$NO_2$, $CH_2OR(23)$, CO—R(24) or O—R(25);

R(23) is hydrogen or alkyl having 1, 2, 3 or 4 carbon atoms;

R(24) is hydrogen, alkyl having 1, 2, 3 or 4 carbon atoms, OR(26) or phenyl; which is unsubstituted or substituted by 1, 2 or 3 identical or different radicals from the series consisting of F, Cl, Br, I, $CF_3$, methyl, methoxy or hydroxyl;

R(26) is hydrogen or alkyl having 1, 2, 3 or 4 carbon atoms;

R(25) is hydrogen, alkyl having 1, 2, 3 or 4 carbon atoms, phenyl, which is unsubstituted or substituted by 1, 2 or 3 identical or different radicals from the series consisting of F, Cl, Br, I, $CF_3$, methyl, methoxy or hydroxyl; or R(25) is heteroaryl having 1, 2, 3, 4, 5, 6, 7, 8 or 9 carbon atoms, which is unsubstituted or substituted by 1, 2 or 3 identical or different radicals from the series consisting of F, Cl, Br, I, $CF_3$, $CH_3$, methoxy; or R(2) and R(3) independently of one another are alkyl having 1, 2, 3 or 4 carbon atoms, cycloalkyl having 3, 4, 5, 6 or 7 carbon atoms, or —$C_dH_{2d}$-phenyl, where the phenyl moiety is unsubstituted or substituted by 1, 2 or 3 identical or different radicals from the series consisting of F, Cl, Br, I, $CF_3$, methyl, methoxy or hydroxyl;

d is zero or 1; or

R(2) and R(3) independently of one another are heteroaryl having 1, 2, 3, 4, 5, 6, 7, 8 or 9 carbon atoms, which is unsubstituted or substituted by 1, 2 or 3 identical or different radicals from the series consisting of F, Cl, Br, I, $CF_3$, $CH_3$, methoxy or hydroxyl; or R(2) and R(3) independently of one another are —$SO_f$—R(37);

R(37) is alkyl having 1, 2, 3 or 4 carbon atoms, cycloalkyl having 3, 4, 5, 6 or 7 carbon atoms, —$C_gH_{2g}$-phenyl, where the phenyl moiety is unsubstituted or substituted by 1, 2 or 3 identical or different radicals from the series consisting of F, Cl, Br, I, $CF_3$, methyl, methoxy or hydroxyl;

f is zero, 1 or 2;

g is zero or 1;

R(4) is hydrogen, alkyl having 1, 2, 3 or 4 carbon atoms, 1-naphthyl, 2-naphthyl, —$C_iH_{2i}$-cycloalkyl having 3, 4, 5, 6 or 7 carbon atoms or —$C_iH_{2i}$-phenyl, where the phenyl moiety is unsubstituted or substituted by 1, 2 or 3 identical or different radicals from the series consisting of alkyl having 1, 2, 3, 4, 5, 6, 7 or 8 carbon atoms, F, Cl, $CF_3$, $SO_jR(48)$, OR(49), NR(50)R(51), —CN or CO—R(52);

i is zero, 1 or 2;

R(48) is alkyl having 1, 2, 3 or 4 carbon atoms or NR(53)R(54), R(53) and R(54) independently of one another are hydrogen, methyl or ethyl;

j is zero or 2;

R(49) is hydrogen or alkyl having 1, 2, 3 or 4 carbon atoms;

R(50) and R(51) independently of one another are hydrogen, methyl or ethyl;

R(52) is hydrogen, alkyl having 1, 2, 3 or 4 carbon atoms or OR(55); R(55) is hydrogen, alkyl having 1, 2, 3 or 4 carbon atoms; or R(4) and R(6) together with the carbon atom carrying them are cycloalkyl having 3, 4, 5, 6 or 7 carbon atoms or fluorenyl;

R(5), R(6), R(7) and R(8) independently of one another are hydrogen, F, $CF_3$, O—R(56), alkyl having 1, 2, 3 or 4 carbon atoms, cycloalkyl having 3, 4, 5, 6 or 7 carbon atoms, —$C_kH_{2k}$-phenyl, where the phenyl moiety is unsubstituted or substituted by 1, 2 or 3 identical or different radicals from the series consisting of F, Cl, Br, I, $CF_3$, methyl, methoxy or hydroxyl;

k is zero or 1;

R(56) is hydrogen, alkyl having 1, 2, 3 or 4 carbon atoms, or phenyl, which is unsubstituted or substituted by 1, 2 or 3 identical or different radicals from the series consisting of F, Cl, Br, I, $CF_3$, methyl, methoxy or hydroxyl, or or R(56) is heteroaryl having 1, 2, 3, 4, 5, 6, 7, 8 or 9 carbon atoms, which is unsubstituted or substituted by 1, 2 or 3 identical or different radicals from the series consisting of F, Cl, Br, I, $CF_3$, $CH_3$, methoxy or hydroxyl; or R(5) and R(7) together are a second bond between the carbon atoms carrying the radicals R(6) and R(8), where R(4), R(6), R(8) are as defined above;

R(9) is alkyl having 1, 2, 3 or 4 carbon atoms, alkenyl having 2, 3 or 4 carbon atoms; or —$C_lH_{2l-ll}$—A;

ll is zero or 2; and l is zero, 1, 2 or 3;
  where l is unequal to zero or 1, when ll is equal to 2;

R(10) is hydrogen;
  alkyl having 1, 2, 3 or 4 carbon atoms; or
  alkenyl having 2, 3 or 4 carbon atoms;

—$C_mH_{2m-mm}$—B, mm is zero or 2; and m is zero, 1, 2, or 3;
  where m is unequal to zero or 1, when mm is equal to 2;

R(11) and R(12) independently of one another are hydrogen or alkyl having 1, 2, 3 or 4 carbon atoms;

z is carbonyl or sulfonyl;

A and B independently of one another are
1. phenyl;
2. a radical as defined in 1, substituted by 1, 2 or 3 identical or different radicals from the series consisting of alkyl having 1, 2, 3 or 4 carbon atoms, F, Cl, $CF_3$, $SO_nR(63)$, OR(64), —CN or CO—R(67);
3. 1-naphthyl or 2-naphthyl;
4. a radical as defined in 3, substituted by 1, 2 or 3 identical or different radicals from the series consisting of alkyl having 1, 2, 3 or 4 carbon atoms, F, Cl, $CF_3$, $CH_3$, methoxy or hydroxyl;
5. heteroaryl having 1, 2, 3, 4, 5, 6, 7, 8 or 9 carbon atoms;
6. a radical as defined in 5, substituted by 1, 2 or 3 identical or different radicals from the series consisting of alkyl having 1, 2, 3 or 4 carbon atoms, F, Cl, $CF_3$, $CH_3$, methoxy or hydroxyl;
7. cycloalkyl having 3, 4, 5, 6 or 7 carbon atoms;
8. O—R(70); or
9. O—R(71);
  n is zero, one or two;
  R(70) and R(71) independently of one another are
1. hydrogen;
2. alkyl having 1, 2, 3 or 4 carbon atoms;
3. —$C_oH_{2o-oo}$-phenyl,
  oo is zero or 2; and
  o is zero, 1,2 or 3;
    where o is unequal to zero or 1, when oo is equal to 2;
4. a radical as defined in 3, where the phenyl moiety is substituted by 1, 2 or 3 identical or different radicals from the series consisting of alkyl having 1, 2, 3 or 4 carbon atoms, F, Cl, CF3, $SO_pR(72)$, OR(73), —CN, —$NO_2$ or CO—R(76); or
5. alkenyl having 2, 3 or 4 carbon atoms;
  R(63) and R(72) independently of one another are alkyl having 1, 2, 3 or 4 carbon atoms or NR(77) R(78); as defined above
  R(67) and R(76) independently of one another are alkyl having 1, 2, 3 or 4 carbon atoms or O-alkyl having 1, 2, 3 or 4 carbon atoms;
  R(64) and R(73) independently of one another are hydrogen or alkyl having 1, 2, 3 or 4 carbon atoms;
p is zero, 1 or 2;

R(13), R(14) and R(15) independently of one another are hydrogen, alkyl having 1, 2, 3 or 4 carbon atoms, F, Cl, $CF_3$, —CN, $SO_q$—R(79), CO—R(80) or O—R(81);
q is zero, 1 or 2;

R(79) is alkyl having 1, 2, 3 or 4 carbon atoms or phenyl, which is unsubstituted or substituted by 1, 2 or 3 identical or different radicals from the series consisting of F, Cl, $CF_3$, methyl, methoxy or hydroxyl;

R(80) is hydrogen, alkyl having 1, 2, 3 or 4 carbon atoms or OR(84); R(84) is hydrogen or alkyl having 1, 2, 3 or 4 carbon atoms;

R(81) is hydrogen, alkyl having 1, 2, 3 or 4 carbon atoms or phenyl, which is unsubstituted or substituted by 1, 2 or 3 identical or different radicals from the series consisting of F, Cl, $CF_3$, methyl, methoxy or hydroxyl;

Y is CR(16)R(17), CO, S, $SO_2$, O or NR(18);

R(16) is hydrogen or —OR(85);
  R(85) is hydrogen or alkyl having 1, 2, 3 or 4 carbon atoms or COR(86);
  R(86) is alkyl having 1, 2, 3 or 4 carbon atoms or phenyl, which is unsubstituted or substituted by 1, 2 or 3 identical or different radicals from the series consisting of F, Cl, $CF_3$, methyl or methoxy;

R(17) is hydrogen or alkyl having 1, 2, 3 or 4 carbon atoms;

R(18) is hydrogen or alkyl having 1, 2, 3 or 4 carbon atoms, COR(87) or $SO_2R(88)$;
  R(87) and R(88) independently of one another are alkyl having 1, 2, 3 or 4 carbon atoms, cycloalkyl having 3, 4, 5, 6, 7 or 8 carbon atoms or phenyl, which is unsubstituted or substituted by 1, 2 or 3 identical or different radicals from the series consisting of F, Cl, Br, I, $CF_3$, methyl or methoxy;

and their physiologically tolerable salts.

Preferred compounds of the formula I are those in which:

X is equal to

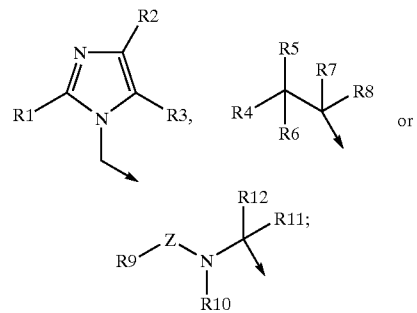

R(1) is hydrogen, alkyl having 1, 2, 3 or 4 carbon atoms or phenyl, which is unsubstituted or substituted by a radical from the series consisting of F, Cl, $CF_3$, methyl, methoxy or hydroxyl; or R(1) is heteroaryl having 1, 2, 3, 4, 5, 6, 7, 8 and 9 carbon atoms, which is unsubstituted or substituted by a radical from the series consisting of F, Cl, $CF_3$, $CH_3$, methoxy or hydroxyl; or R(1) is cycloalkyl having 3, 4, 5, 6 or 7 carbon atoms;

R(2) and R(3) independently of one another are hydrogen, F, Cl, $CF_3$, —CN, —$NO_2$, CO—R(24) or O—R(25),
  R(24) is hydrogen, alkyl having 1, 2, 3 or 4 carbon atoms, OR(26) or phenyl, which is unsubstituted or substituted by a substituent from the series consisting of F, Cl, $CF_3$, methyl, methoxy or hydroxyl,
  R(26) is hydrogen or alkyl having 1, 2, 3 or 4 carbon atoms,
  R(25) is hydrogen, alkyl having 1, 2, 3 or 4 carbon atoms, phenyl, which is unsubstituted or substituted by a substituent from the series consisting of F, Cl, CF$_3$, methyl, methoxy or hydroxyl, or R(2) and R(3) independently of one another are alkyl having 1, 2, 3 or 4 carbon atoms, cycloalkyl having 3, 4, 5, 6 or 7 carbon atoms or phenyl, which is unsubstituted or substituted by a substituent from the series consisting of F, Cl, CF$_3$, methyl, methoxy or hydroxyl; or R(2) and R(3) independently of one another are heteroaryl having 1, 2, 3, 4, 5, 6, 7, 8 or 9 carbon atoms, which is unsubstituted or substituted by 1, 2 or 3 identical or different radicals from the series consisting of F, Cl, CF$_3$, CH$_3$, methoxy or hydroxyl; or R(2) and R(3) independently of one another are —SO$_f$—R(37),
R(37) is alkyl having 1, 2, 3 or 4 carbon atoms, cycloalkyl having 3, 4, 5, 6 or 7 carbon atoms or phenyl, which is unsubstituted or substituted by a radical from the series consisting of F, Cl, CF$_3$, methyl, methoxy or hydroxyl;
f is zero or 2;

R(4) is methyl, ethyl, 1-naphthyl, 2-naphthyl, cycloalkyl having 3, 4, 5, 6 or 7 carbon atoms or —C$_i$H$_{2i}$-phenyl,
i is zero or 1; or R(4) and R(6) together with the carbon atom carrying them are cycloalkyl having 3, 4, 5, 6 or 7 carbon atoms or fluorenyl;

R(5) and R(7) independently of one another are hydrogen or fluorine; or together are a second bond between the carbon atoms carrying the radicals R(6) and R(8);

R(6) and R(8) independently of one another are hydrogen, F, CF$_3$, O—R(56), alkyl having 1, 2, 3 or 4 carbon atoms, —C$_k$H$_{2k}$-phenyl, where the phenyl moiety is unsubstituted or substituted by 1, 2 or 3 identical or different radicals from the series consisting of F, Cl, CF$_3$, methyl, methoxy or hydroxyl;
k is zero or 1
R(56) is hydrogen, alkyl having 1, 2, 3 or 4 carbon atoms, or phenyl, which is unsubstituted or substituted by 1, 2 or 3 identical or different radicals from the series consisting of F, Cl, CF$_3$, methyl, methoxy or hydroxyl; or
R(56) is heteroaryl having 1, 2, 3, 4, 5, 6, 7, 8 or 9 carbon atoms, which is unsubstituted or substituted by 1, 2 or 3 identical or different radicals from the series consisting of F, Cl, CF$_3$, CH$_3$, methoxy or hydroxyl;

R(9)
is alkyl having 1, 2, 3 or 4 carbon atoms;
alkenyl having 2, 3 or 4 carbon atoms; or —C$_l$H$_{2l-ll}$—A;
ll is zero or 2; and
l is zero, 1, 2 or 3;
where l is unequal to zero or 1, when ll is equal to 2;

R(10) is hydrogen;
alkyl having 1, 2, 3 or 4 carbon atoms;
alkenyl having 2, 3 or 4 carbon atoms; or —C$_m$H$_{2m-mm}$—B,
mm is zero or 2; and
m is zero, 1, 2 or 3;
where m is unequal to zero or 1, when mm is equal to 2;

R(11) and R(12) independently of one another are hydrogen or methyl;

Z is carbonyl or sulfonyl;

A and B independently of one another are
1. phenyl;
2. a radical as defined in 1, substituted by 1, 2 or 3 identical or different radicals from the series consisting of alkyl having 1, 2, 3 or 4 carbon atoms, F, Cl, CF$_3$, SO$_2$R(63), OR(64), —CN or CO—R(67);
3. 1-naphthyl or 2-naphthyl;
4. a radical as defined in 3, substituted by a radical from the series consisting of alkyl having 1, 2, 3 or 4 carbon atoms, F, Cl, CF$_3$, CH$_3$, methoxy or hydroxyl;
5. heteroaryl having 1, 2, 3, 4, 5, 6, 7, 8 or 9 carbon atoms;
6. a radical as defined in 5, substituted a radical from the series consisting of F, Cl, CF$_3$, CH$_3$, methoxy or hydroxyl;
7. cycloalkyl having 3, 4, 5, 6 or 7 carbon atoms;
R(63) is alkyl having 1, 2, 3 or 4 carbon atoms;
R(67) is alkyl having 1, 2, 3 or 4 carbon atoms or O-alkyl having 1, 2, 3 or 4 carbon atoms;
R(64) is hydrogen or alkyl having 1, 2, 3 or 4 carbon atoms;

R(13), R(14) and R(15) independently of one another are hydrogen, alkyl having 1, 2, 3 or 4 carbon atoms, F, Cl, CF$_3$, —CN, SO$_q$—R(79), CO—R(80) or O—R(81);
q is zero or 2,
R(79) is alkyl having 1, 2, 3 or 4 carbon atoms or phenyl, which is unsubstituted or substituted by 1, 2 or 3 identical or different radicals from the series consisting of F, Cl, CF$_3$, methyl, methoxy or hydroxyl;
R(80) is hydrogen, alkyl having 1, 2, 3 or 4 carbon atoms or OR(84);
R(84) is hydrogen or alkyl having 1, 2, 3 or 4 carbon atoms;
R(81) is hydrogen, alkyl having 1, 2, 3 or 4 carbon atoms or phenyl, which is unsubstituted or substituted by 1, 2 or 3 identical or different radicals from the series consisting of F, Cl, CF$_3$, methyl, methoxy or hydroxyl;

Y is CR(16)R(17), CO, S, S$_2$, O, NR(18);
R(16) is hydrogen or OR(85),
R(85) is hydrogen or alkyl having 1, 2, 3 or 4 carbon atoms or COR(86);
R(86) is alkyl having 1, 2, 3 or 4 carbon atoms or phenyl, which is unsubstituted or substituted by a radical from the series consisting of F, Cl, CF$_3$, methyl or methoxy;
R(17) is hydrogen or alkyl having 1, 2, 3 or 4 carbon atoms;
R(18) is hydrogen or alkyl having 1, 2, 3 or 4 carbon atoms, COR(87) or SO$_2$R(88),
R(87), R(88) independently of one another are alkyl having 1, 2, 3 or 4 carbon atoms, cycloalkyl having 3, 4, 5 or 6 carbon atoms or phenyl, which is unsubstituted or substituted by a radical from the series consisting of F, Cl, Br, I, CF$_3$, methyl or methoxy;

and their physiologically tolerable salts.

Particularly preferred compounds of the formula I are those in which:

X is equal to

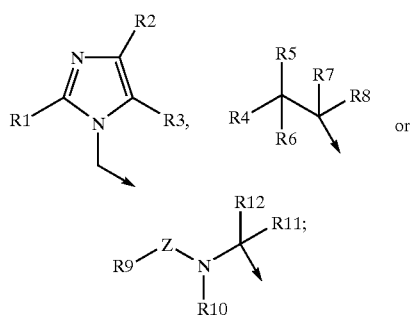

or

R(1) is alkyl having 1, 2, 3 or 4 carbon atoms or phenyl, which is unsubstituted or substituted by a radical from the series consisting of F, Cl, CF$_3$, methyl or methoxy; or R(1) is heteroaryl having 1, 2, 3, 4, 5, 6, 7, 8 or 9 carbon atoms, which is unsubstituted or substituted by a radical from the series consisting of F, Cl, CF$_3$, CH$_3$ or methoxy; or R(1) is cycloalkyl having 3, 4, 5, 6 or 7 carbon atoms;

R(2) and R(3) independently of one another are hydrogen, F, Cl, CF$_3$, —CN, CO—R(24) or O—R(25);
R(24) is hydrogen, alkyl having 1, 2, 3 or 4 carbon atoms, OR(26) or phenyl, which is unsubstituted or substituted by a radical from the series consisting of F, Cl, CF$_3$, methyl or methoxy; R(26) is hydrogen, methyl or ethyl;
R(25) is hydrogen, alkyl having 1, 2, 3 or 4 carbon atoms, or phenyl, which is unsubstituted or substituted by a radical from the series consisting of F, Cl, CF$_3$, methyl or methoxy; or
R(25) is heteroaryl having 1, 2, 3, 4, 5, 6, 7, 8 or 9 carbon atoms, which is unsubstituted or substituted by a radical from the series consisting of F, Cl, CF$_3$, CH$_3$ or methoxy; or R(2) and R(3) independently of one another are alkyl having 1, 2, 3 or 4 carbon atoms, cycloalkyl having 3, 4, 5, 6 or 7 carbon atoms, or phenyl, which is unsubstituted or substituted by a radical from the series consisting of F, Cl, CF$_3$, methyl or methoxy; or R(2) and R(3) independently of one another are heteroaryl having 1, 2, 3, 4, 5, 6, 7, 8 or 9 carbon atoms, which is unsubstituted or substituted by a radical from the series consisting of F, Cl, CF$_3$, CH$_3$ or methoxy; or R(2) and R(3) independently of one another are —SO$_f$—R(37);
R(37) is alkyl having 1, 2, 3 or 4 carbon atoms or phenyl, which is unsubstituted or substituted by a radical from the series consisting of F, Cl, CF$_3$, methyl or methoxy;
f is zero or 2;

R(4) is methyl, ethyl, 1-naphthyl, 2-naphthyl, cycloalkyl having 3, 4, 5, 6 or 7 carbon atoms or phenyl;

R(4) and R(6) together with the carbon atom carrying them are cycloalkyl having 3, 4, 5, 6 or 7 carbon atoms or fluorenyl;

R(5) and R(7) independently of one another are hydrogen or together are a second bond between the carbon atoms carrying the radicals R(6) and R(8);

R(6) and R(8) independently of one another are hydrogen, CF$_3$, O—R(56), alkyl having 1, 2, 3 or 4 carbon atoms or phenyl, where phenyl is unsubstituted or substituted by a radical from the series consisting of F, Cl, CF$_3$, methyl or methoxy;
R(56) is hydrogen, alkyl having 1, 2, 3 or 4 carbon atoms, or phenyl, which is unsubstituted or substituted by a radical from the series consisting of F, Cl, CF$_3$, methyl or methoxy; or or
R(56) is heteroaryl having 1, 2, 3, 4, 5, 6, 7, 8 or 9 carbon atoms, which is unsubstituted or substituted by a radical from the series consisting of F, Cl, CF$_3$, CH$_3$ or methoxy;

R(9)
is alkyl having 1, 2, 3 or 4 carbon atoms;
alkenyl having 2, 3 or 4 carbon atoms; or —C$_I$H$_{2I-II}$—A,
II is zero or 2; and
I is zero, 1, 2 or 3;
where I is unequal to zero or 1, when II is equal to 2;

R(10) is hydrogen;
alkyl having 1, 2, 3 or 4 carbon atoms;
alkenyl having 2, 3 or 4 carbon atoms; or —C$_m$H$_{2m-mm}$—B,
mm is zero or 2; and
m is zero, 1, 2 or 3;
where m is unequal to zero or 1, when mm is equal to 2;

R(11) and R(12) independently of one another are hydrogen or methyl;

Z is carbonyl or sulfonyl;

A and B independently of one another are
1. phenyl;
2. a radical as defined in 1, substituted by a radical from the series consisting of alkyl having 1, 2, 3 or 4 carbon atoms, F, Cl, CF$_3$, SO$_2$R(63), OR(64), —CN or CO—R(67);
3. 1-naphthyl or 2-naphthyl;
4. a radical as defined in 3, substituted by a radical from the series consisting of alkyl having 1, 2, 3 or 4 carbon atoms, F, Cl, CF$_3$, CH$_3$ or methoxy;
5. heteroaryl having 1, 2, 3, 4, 5, 6, 7, 8 or 9 carbon atoms;
6. a radical as defined in 5, substituted by a radical from the series consisting of F, Cl, CF$_3$, CH$_3$ or methoxy;
7. cycloalkyl having 3, 4, 5, 6 or 7 carbon atoms;
R(63) is alkyl having 1, 2, 3 or 4 carbon atoms;
R(64) is hydrogen or alkyl having 1, 2, 3 or 4 carbon atoms;
R(67) is alkyl having 1, 2, 3 or 4 carbon atoms or O-alkyl having 1, 2, 3 or 4 carbon atoms;

R(13), R(14) and R(15) independently of one another are hydrogen, methyl, F, Cl, CF$_3$, —CN, SO$_2$—R(79), CO—R(80) or O—R(81);
R(79) is alkyl having 1, 2, 3 or 4 carbon atoms or phenyl, which is unsubstituted or substituted by a radical from the series consisting of F, Cl, CF$_3$, methyl or methoxy;
R(80) is hydrogen, methyl or OR(84); R(84) is hydrogen or alkyl having 1, 2, 3 or 4 carbon atoms;
R(81) is hydrogen, alkyl having 1, 2, 3 or 4 carbon atoms or phenyl, which is unsubstituted or substituted by a radical from the series consisting of F, Cl, CF$_3$, methyl or methoxy;

Y is CR(16)R(17), CO, S or SO$_2$;

R(16) is hydrogen or —OR(85);
  R(85) is hydrogen, methyl or COR(86);
  R(86) is methyl, cyclopentyl, cyclohexyl or phenyl, which is unsubstituted or substituted by a radical from the series consisting of F, Cl, CF$_3$, methyl or methoxy;
R(17) is hydrogen or methyl;
and their physiologically tolerable salts.

Particularly preferred compounds of the formula I are those in which:
X is

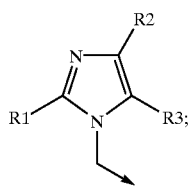

R(1) is alkyl having 1, 2, 3 or 4 carbon atoms or phenyl, which is unsubstituted or substituted by a radical from the series consisting of F, Cl, CF$_3$, methyl or methoxy;
R(2) and R(3) independently of one another are hydrogen, F, Cl, CF$_3$, —CN, CO—R(24) or O—R(25),
  R(24) is hydrogen, alkyl having 1, 2, 3 or 4 carbon atoms, OR(26) or phenyl, which is unsubstituted or substituted by a radical from the series consisting of F, Cl, CF$_3$, methyl or methoxy;
  R(26) is hydrogen, methyl or ethyl;
  R(25) is hydrogen, alkyl having 1, 2, 3 or 4 carbon atoms, phenyl, which is unsubstituted or substituted by a radical from the series consisting of F, Cl, CF$_3$, methyl or methoxy; or
  R(25) is heteroaryl, which is unsubstituted or substituted by a radical from the series consisting of F, Cl, CF$_3$, CH$_3$ or methoxy;
R(2) and R(3) independently of one another are alkyl having 1, 2, 3 or 4 carbon atoms, cycloalkyl having 3, 4, 5, 6 or 7 carbon atoms; or
R(2) and R(3) independently of one another are phenyl, which is unsubstituted or substituted by a radical from the series consisting of F, Cl, CF$_3$, methyl or methoxy; or
R(2) and R(3) independently of one another are heteroaryl having 1, 2, 3, 4, 5, 6, 7, 8 or 9 carbon atoms, which is unsubstituted or substituted by a radical from the series consisting of F, Cl, CF$_3$, CH$_3$ or methoxy; or
R(2) and R(3) independently of one another are —SO$_f$—R(37),
  R(37) is alkyl having 1, 2, 3 or 4 carbon atoms or phenyl, which is unsubstituted or substituted by a radical from the series consisting of F, Cl, CF$_3$, methyl or methoxy;
  f is zero or 2;
R(13), R(14) and R(15) independently of one another are hydrogen, methyl, F, Cl, CF$_3$, —CN, SO$_2$—R(79), CO—R(80) or O—R(81);
  R(79) and R(81) independently of one another are alkyl having 1, 2, 3 or 4 carbon atoms or phenyl, which is unsubstituted or substituted by a radical from the series consisting of F, Cl, CF$_3$, methyl or methoxy;
  R(80) is hydrogen, methyl or OR(84);
  R(84) is hydrogen or alkyl having 1, 2, 3 or 4 carbon atoms;
Y is methylene;
and their physiologically tolerable salts.

Preferred compounds are also those of the formula I, in which Y is methylene and X, R13, R14 and R15 are as defined above, and their physiologically tolerable salts. Compounds of the formula I are furthermore preferred in which R(13), R(14) and R(15) are in each case hydrogen, and their physiologically tolerable salts.

Both alkyl and alkenyl can, independently of one another, be straight-chain or branched.

Examples of alkyl radicals having 1, 2, 3, 4, 5, 6, 7 or 8 carbon atoms are:
methyl, ethyl, propyl, butyl, pentyl, hexyl, heptyl, octyl, isopropyl, isobutyl, isopentyl, neopentyl, isohexyl, 3-methylpentyl, sec-butyl, tert-butyl, tert-pentyl.

Examples of alkenyl radicals are vinyl, 1-propenyl, allyl, butenyl, 3-methyl-2-butenyl.

Cycloalkyl is also understood as meaning alkyl-substituted rings.

Cycloalkyl radicals are in particular cyclopropyl, cyclobutyl, cyclopentyl, cyclohexyl, cycloheptyl, but which can also be substituted, for example, by alkyl having 1, 2, 3 or 4 carbon atoms. Examples of substituted cycloalkyl radicals which may be mentioned are 4-methylcyclohexyl and 2,3-dimethylcyclopentyl.

Aryl groups having 6, 7, 8, 9, 10, 11, 12, 13 or 14 carbon atoms are, for example, phenyl, naphthyl, biphenyl, antryl or fluorenyl, where 1-naphthyl, 2-naphthyl and in particular phenyl are preferred.

Heteroaryl having 1, 2, 3, 4, 5, 6, 7, 8 or 9 carbon atoms is understood as meaning, in particular, radicals which are derived from phenyl or naphthyl, in which one or more CH groups are replaced by N and/or in which at least two adjacent CH groups are replaced by S, NH or O (with formation of a five-membered aromatic ring). In addition, one or both atoms of the condensation site of bicyclic radicals can also be nitrogen atoms (such as in indolizinyl).

Heteroaryl is, in particular, furanyl, thienyl, pyrrolyl, imidazolyl, pyrazolyl, triazolyl, tetrazolyl, oxazolyl, isoxazolyl, thiazolyl, isothiazolyl, pyridyl, pyrazinyl, pyrimidinyl, pyridazinyl, indolyl, indazolyl, quinolyl, isoquinolyl, phthalazinyl, quinoxalinyl, quinazolinyl, cinnolinyl.

Halogen is fluorine, chlorine, bromine or iodine, preferably fluorine or chlorine.

The present invention includes all stereoisomeric forms of the compounds of the formula I. Asymmetric centers contained in the compounds of the formula I can all independently of one another have the S configuration or the R configuration. The invention includes all possible enantiomers and diastereomers, as well as mixtures of two or more stereoisomeric forms, for example mixtures of enantiomers and/or diastereomers, in all ratios. The invention thus relates to enantiomers in enantiomerically pure form, both as levorotatory and dextrorotatory antipodes, in the form of racemates and in the form of mixtures of the two enantiomers in all ratios. In the presence of cis/trans isomerism, the invention relates both to the cis form and trans form and mixtures of these forms in all ratios. Individual stereoisomers can be prepared, if desired, by resolution of a mixture according to customary methods, for example by chromatography or crystallization, by use of stereochemically uniform starting substances in the synthesis or by stereoselective synthesis. If appropriate, derivatization can be carried out before separation of stereoisomers. A stereoisomer mixture can be separated at the stage of the compounds of the formula I or at the stage of an intermediate in the course of the synthesis. In the presence of mobile hydrogen atoms, the present invention also includes all tautomeric forms of the compounds of the formula I.

If the compounds of the formula I contain one or more acidic or basic groups, the invention also relates to the corresponding physiologically or toxicologically tolerable salts, in particular the pharmaceutically utilizable salts. Thus the compounds of the formula I which contain acidic groups can be present and used according to the invention, for example, as alkali metal salts, alkaline earth metal salts or as ammonium salts. Examples of such salts are sodium salts, potassium salts, calcium salts, magnesium salts or salts with ammonia or organic amines such as, for example, ethylamine, ethanolamine, triethanolamine or amino acids. Compounds of the formula I which contain one or more basic, that is protonatable, groups can be present and used according to the invention in the form of their acid addition salts with physiologically tolerable inorganic or organic acids, for example as salts with hydrogen chloride, hydrogen bromide, phosphoric acid, sulfuric acid, nitric acid, methanesulfonic acid, p-toluenesulfonic acid, napthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfamic acid, phenylpropionic acid, gluconic acid, ascorbic acid, isonicotinic acid, citric acid, adipic acid, etc. If the compounds of the formula I simultaneously contain acidic and basic groups in the molecule, the invention also includes internal salts or betaines (zwitterions) in addition to the salt forms described. Salts can be obtained from the compounds of the formula I by customary processes known to the person skilled in the art, for example by combination with an organic or inorganic acid or base in a solvent or dispersant, or alternatively from other salts by anion exchange or cation exchange. The present invention also includes all salts of the compounds of the formula I which are not directly suitable for use in pharmaceuticals because of low physiological tolerability, but are suitable, for example, as intermediates for chemical reactions or for the preparation of physiologically tolerable salts. Physiologically tolerable salts of compounds of the formula (I) are understood as meaning, for example, their organic and inorganic salts, such as are described in Remington's Pharmaceutical Sciences (17th Edition, page 1418 (1985)). On account of their physical and chemical stability and their solubility, sodium, potassium, calcium and ammonium salts, inter alia, are preferred for acidic groups; salts of hydrochloric acid, sulfuric acid, phosphoric acid or of carboxylic acids or sulfonic acids, such as, for example, acetic acid, citric acid, benzoic acid, maleic acid, fumaric acid, tartaric acid and p-toluenesulfonic acid, inter alia, are preferred for basic groups.

The present invention furthermore includes all solvates of compounds of the formula I, for example hydrates or adducts with alcohols, and also derivatives of the compounds of the formula I such as, for example, esters, and prodrugs and active metabolites.

The invention also relates to a process for the preparation of the novel compounds of the formula (I), and their physiologically tolerable salts, which comprises reacting compounds of the formula (II)

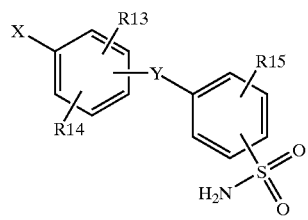

in which the radicals are as defined above, with cyanogen bromide. The reaction is carried out in a dipolar aprotic solvent which is stable to cyanogen bromide, for example acetonitrile, DMA, TMU or NMP using a strong auxiliary base which is not very nucleophilic, such as, for example, $K_2CO_3$ or $Cs_2CO_3$. A suitable reaction temperature is a temperature between 0° C. and the boiling point of the solvent used; a temperature between 60° C. and 120° C. is preferred.

Sulfonamide derivatives of the formula II with X equal to can be prepared by reacting compounds of the formula III in which Y, R(13), R(14) and R(15) are as defined above and G is, for example, $CH_2Cl$, $CH_2Br$, $CH_2OH$, $CH_2OMs$ and the sulfonamide group is advantageously present in protected form, for example as a dimethylaminomethylene derivative, in a manner known from the literature (nucleophilic substitution or Mitsunobu reaction, cf. J. Med. Chem. 1995, 38, 2357) with compounds of the formula IV Processes for the preparation of compounds of the formula IV are known, inter alia, from EP-A 253310, EP-A 324377, U.S. Pat. No. 5,482,957 and J. Med. Chem. 1995, 38, 2357–2377.

Sulfonamide derivatives of the formula II where X is equal to

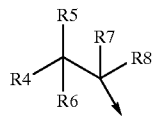

are accessible, for example, via Wittig reactions of compounds of the formula II, in which G is —(CO)R(8) and Y, R(8), R(13), R(14) and R(15) are as defined above, with a phosphorane, which contains the radicals R(4) and/or R(5) and/or R(6). Such Wittig reactions are known to the person skilled in the art and are described, for example, in Org. Synth. 1960, 40, 66; J. Org. Chem. 1963, 28,1128 and Org. Synth. Coll. Vol. 5 1973, 751.

Sulfonamide derivatives of the formula II where X is equal to

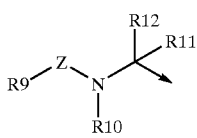

are accessible, for example, via compounds of the formula III where G is equal to formyl by preparing the amine by reductive amination with $NaBH_3CN$ (Synthesis 1975, 135), then reacting it with an acid chloride R(9)-Z—Cl. If R(11), R(12) are unequal to hydrogen, it is necessary to introduce the radicals concerned. This is carried out either by reacting the imine which is passed through in the reductive amination not with a reductant, but with an organometallic compound carrying the radical R(11) or the radical R(12), such as, for example, a Grignard compound or an alkyllithium compound in a manner known to the person skilled in the art.

Compounds of the formula III, in which Y is as defined above, can be prepared by methods known from the literature by allowing suitable aryl derivatives, which are substituted, for example, by methyl, carboxylic acid ester, formyl, from which the abovementioned radicals G can be obtained by processes known to the person skilled in the art, for example in situ generated benzylzinc derivatives (cf. J. Org. Chem. 1977, 42, 1821; J. Org. Chem. 1988, 53, 5789) with substituted aryl halides under Pd(0) catalysis [Y=methylene]. Corresponding aryllithium derivatives react with substituted benzaldehydes or benzoyl chlorides to give substituted diphenylmethane or benzophenone derivatives [Y=C(R(16)R(17), CO]. The preparation of the ethers and thioether derivatives [Y=O, S, $SO_2$] is conventionally carried out via nucleophilic substitution of sulfonamide-activated halobenzenes with phenolates or thiophenolates, where the latter can be converted into the corresponding sulfonyl compounds by subsequent oxidation, for example with meta-chloroperbenzoic acid. The substituted diphenylamines [Y=NR(18)] can likewise be obtained by methods known from the literature via Pd(0)-catalyzed reaction of anilines with aryl halides (J. Org. Chem. 1996, 61, 1133), or by reaction of acylated anilines with aryl halides in the presence of potassium carbonate and copper(l) iodide (J. Org. Chem. 1978, 26, 4975).

The compounds of the formula I according to the invention are suitable as inhibitors of the sodium-dependent bicarbonate/chloride exchanger (NCBE) or of the sodium/bicarbonate symporter.

EP-A 855392 describes imidazole derivatives having a biphenylsulfonylcyanamide side chain as NCBE inhibitors.

EP-A 903339 and DE 19804251.5 propose substituted biphenylsulfonylcyanamide derivatives as NCBE inhibitors.

Compounds similar to the compounds of the formula I according to the invention are disclosed in the U.S. Pat. Nos. 5,482,957 and 5,604,251 as well as EP-A 479479, where these are described as hypotensive angiotensin II antagonists. However, they do not have the sulfonylcyanamide side chain which is always present according to the invention. Imidazolebiphenyl derivatives are also described in WO9523792, WO9523791, EP-A 465368, EP-A 648763. The known compounds are angiotensin II receptor antagonists of the subtype AT1, which action is not present in the compounds I according to the invention or only to a slight extent.

In addition, the invention relates to the use of a compound of the formula I for the production of a medicament for the treatment or prophylaxis of illnesses caused by ischemic conditions;

and the use of a compound of the formula I for the production of a medicament for the treatment or prophylaxis of cardiac infarct;

and the use of a compound of the formula I for the production of a medicament for the treatment or prophylaxis of angina pectoris;

and the use of a compound of the formula I for the production of a medicament for the treatment or prophylaxis of ischemic conditions of the heart;

and the use of a compound of the formula I for the production of a medicament for the treatment or prophylaxis of ischemic conditions of the peripheral and central nervous system and of stroke;

and the use of a compound of the formula I for the production of a medicament for the treatment or prophylaxis of ischemic conditions of peripheral organs and members;

and the use of a compound of the formula I for the production of a medicament for the treatment of states of shock;

and the use of a compound of the formula I for the production of a medicament for use in surgical operations and organ transplantations;

and the use of a compound of the formula I for the production of a medicament for the preservation and storage of transplants for surgical measures;

and the use of a compound of the formula I for the production of a medicament for the treatment of illnesses in which cell proliferation is a primary or secondary cause; and thus its use for the production of an antiatherosclerotic, an agent against diabetic late complications, carcinomatous disorders, fibrotic disorders such as pulmonary fibrosis, liver fibrosis or kidney fibrosis, prostate hyperplasia;

and the use of a compound of the formula I for the production of a medicament for the treatment of impaired respiratory drive;

and a pharmaceutical comprising an efficacious amount of a compound of the formula I.

On account of inhibition of the cellular $Na^+$-dependent $Cl^-/HCO_3^-$ exchange mechanism and the antiarrhythmic properties of the compounds of the formula I according to the invention which are potentially connected therewith, which are important, for example, for the treatment of illnesses which occur in the case of oxygen-deficiency symptoms, the compounds of the formula I are suitable as antiarrhythmic pharmaceuticals having a cardioprotective component for infarct prophylaxis and infarct treatment and for the treatment of angina pectoris, where they also inhibit or greatly decrease, in a preventive manner, the pathophysiological processes in the formation of ischemically induced damage, in particular in the elicitation of ischemically induced cardiac arrhythmias.

Because of their potentially protective actions against pathological hypoxic and ischemic situations, the compounds of the formula I according to the invention can be used on account of inhibition of the cellular $Na^+$-dependent $Cl^-/HCO_3^-$ exchange mechanism or of the sodium/bicarbonate symporter as pharmaceuticals for the treatment of all acute or chronic damage caused by ischemia or illnesses induced primarily or secondarily thereby. They can protect organs acutely or chronically undersupplied with oxygen by lowering or preventing ischemically induced damage and are thus suitable as pharmaceuticals, for example, in thromboses, vascular spasms, atherosclerosis or in surgical interventions (e.g. in liver and kidney organ transplantations, where the compounds can be used both for the protection of the organs in the donor before and during removal, for the protection of removed organs, for example during treatment with or storage thereof in physiological bath fluids, and during transfer to the recipient's body) or chronic or acute kidney failure. The compounds of the formula I are also potentially valuable pharmaceuticals having a protective action when carrying out angioplastic surgical interventions, for example on the heart and on peripheral vessels. Corresponding to their potentially protective action against ischemically induced damage, the compounds are also suitable as pharmaceuticals for the treatment of ischemias of the nervous system, in particular of the central nervous system, where they can be used, for example, for the treatment of stroke or of cerebral edema. Moreover, the compounds of the formula I according to the invention are also suitable for the treatment of forms of shock, such as, for example, of allergic, cardiogenic, hypovolemic and of bacterial shock.

On account of a potentially strongly inhibitory action on the proliferation of cells, for example fibroblast cell proliferation and the proliferation of the smooth vascular muscle cells, the compounds of the formula I are suitable as valuable therapeutics for illnesses in which cell proliferation is a primary or secondary cause, and can therefore be used as antiatherosclerotics, agents against diabetic late complications, carcinomatous disorders, fibrotic disorders such as pulmonary fibrosis, liver fibrosis or kidney fibrosis, organ hypertrophies and hyperplasias, in particular in prostate hyperplasia or prostate hypertrophy.

It has been found that inhibitors of the $Na^+$-dependent $Cl^-/HCO_3^-$ exchanger or of the sodium/bicarbonate symporter can stimulate the respiration by means of an increase in the chemosensitivity of the respiratory chemoreceptors. These chemoreceptors are responsible to a considerable extent for the maintenance of an orderly respiratory activity. They are activated in the body by hypoxia, pH decrease and increase in $CO_2$ (hypercapnia) and result in an adjustment of the respiratory minute volume. During sleep, the respiration is particularly susceptible to interference and to a great extent dependent on the activity of the chemoreceptors.

An improvement in the respiratory drive as a result of stimulation of the chemoreceptors with substances which inhibit the $Na^+$-dependent $Cl^-/HCO_3^-$ exchange results in an improvement of the respiration in the following clinical conditions and illnesses: impaired central respiratory drive (e.g. central sleep apnea, sudden infant death, post-operative hypoxia), muscle-related respiratory disorders, respiratory disorders after long-term ventilation, respiratory disorders during adaptation in a high mountain area, obstructive and mixed forms of sleep apneas, acute and chronic lung diseases with hypoxia and hypercapnia.

Pharmaceuticals which contain a compound of the formula I can be administered orally, parenterally, intravenously, rectally or by inhalation, the preferred administration being dependent on the particular symptoms of the disorder. The compounds of the formula I can be used here on their own or together with pharmaceutical auxiliaries, namely both in veterinary and in human medicine.

The person skilled in the art is familiar on the basis of his expert knowledge with the auxiliaries which are suitable for the desired pharmaceutical formulation. In addition to solvents, gel-forming agents, suppository bases, tablet auxiliaries and other active compound excipients, it is possible to use, for example, antioxidants, dispersants, emulsifiers, antifoams, flavor corrigents, preservatives, solubilizers or colorants.

For an oral administration form, the active compounds are mixed with the additives suitable therefor, such as excipients, stabilizers or inert diluents and are brought by means of the customary methods into the suitable administration forms, such as tablets, coated tablets, hard capsules, aqueous, alcoholic or oily solutions. Inert excipients which can be used are, for example, gum arabic, magnesia, magnesium carbonate, potassium phosphate, lactose, glucose or starch, in particular corn starch. Preparation can take place here both as dry and as moist granules. Possible oily excipients or solvents are, for example, vegetable or animal oils, such as sunflower oil or codliver oil.

For subcutaneous or intravenous administration, the active compounds are brought into solution, suspension or emulsion, if desired with the substances customary therefor such as solubilizers, emulsifiers or other auxiliaries. Suitable solvents, for example, are: water, physiological saline solution or alcohols, e.g. ethanol, propanol, glycerol, and additionally also sugar solutions such as glucose or mannitol solutions, or alternatively a mixture of the various solvents mentioned.

Pharmaceutical formulations suitable for administration in the form of aerosols or sprays are, for example, solutions, suspensions or emulsions of the active compound of the formula I in a pharmaceutically acceptable solvent, such as, in particular, ethanol or water, or a mixture of such solvents.

If required, the formulation can also contain other pharmaceutical auxiliaries such as surfactants, emulsifiers and stabilizers, and also a propellant. Such a preparation customarily contains the active compound in a concentration from approximately 0.1 to 10, in particular from approximately 0.3 to 3% by weight.

The dose of the active compound of the formula I to be administered and the frequency of administration depend on the potency and duration of action of the compounds used; additionally also on the nature and severity of the illness to be treated and on the sex, age, weight and individual responsiveness of the mammal to be treated. On average, the daily dose of a compound of the formula I in a patient weighing approximately 75 kg is at least 0.001 mg/kg, preferably 0.01 mg/kg, to at most 10 mg/kg, preferably 1 mg/kg, of body weight. In acute episodes of the disease, for example immediately after suffering a cardiac infarct, even higher and, especially, more frequent doses may also be necessary, e.g. up to 4 individual doses per day. In particular on i.v. administration, for example in the case of an infarct patient in the intensive care unit, up to 200 mg per day may be necessary.

The compounds of the formula I can be employed as sole active compounds or in combination with other pharmacologically active compounds.

The compounds of the formula I and/or their physiologically tolerable salts can also be used to achieve an advantageous therapeutic action together with other pharmacologically active compounds for the treatment or prophylaxis of the abovementioned syndromes, in particular for the treatment of cardiovascular disorders. Combination with inhibitors of the sodium/hydrogen exchanger (NH-E) and/or with active substances from other classes of cardiovascular active compound is preferred.

The invention additionally relates to the combination of a) NCBE inhibitors of the formula I and/or their physiologically tolerable salts with NHE inhibitors and/or their physiologically tolerable salts; b) NCBE inhibitors of the formula I and/or their physiologically tolerable salts with active substances from other classes of cardiovascular active compound and/or their physiologically tolerable salts and c) of NCBE inhibitors of the formula I and/or their physiologically tolerable salts with NHE inhibitors and/or their physiologically tolerable salts and with active substances from other classes of cardiovascular active compound and/or their physiologically tolerable salts.

The active compounds known and identified as NHE inhibitors are guanidine derivatives, preferably acylguanidines, inter alia as are described in Edward J. Cragoe, Jr., "DIURETICS, Chemistry, Pharmacology and Medicine", J. WILEY & Sons (1983), 303–341 or the NHE inhibitors mentioned in EP 98115754.8.

Suitable NHE inhibitors are, for example, also benzoylguanidines, such as are described in U.S. Pat. Nos. 5,292,755, 5,373,024, 5,364,868, 5,591,754, 5,516,805, 5,559,153, 5,571,842, 5,641,792, 5631293, EP-A 577024, EP-A 602522, EP-A 602523, EP-A 603650, EP-A 604852, EP-A 612723, EP-A 627413, EP-A 628543, EP-A 640593, EP-A 640588, EP-A702001, EP-A 713864, EP-A 723956, EP-A 754680, EP-A 765868, EP-A 774459, EP-A 794171, EP-A 814077, EP-A 869116; ortho-substituted benzoylguanidines, such as are described in EP-A 556673, EP-A 791577, EP-A 794172; ortho-amino-substituted benzoylguanidines, such as are described in EP-A 690048; isoquinolines, such as are described in EP-A 590455; benzofused 5-membered ring heterocycles, such as are described in EP-A 639573; diacyl-substituted guanidines, such as are described in EP-A 640587; acylguanidines, such as are described in U.S. Pat. No. 5,547,953; phenyl-substituted alkyl- or alkenylcarbonylguanidines carrying perfluoroalkyl groups, such as are described in U.S. Pat. No. 5567734, EP-A 688766; heteroaroylguanidines, such as are described in EP-A 676395; bicyclic heteroaroylguanidines, such as are described in EP-A 682017; indenoylguanidines, such as are described in EP-A 738712; benzyloxycarbonylguanidines, such as are described in EP-A 748795; phenyl-substituted alkenylcarbonylguanidines carrying fluorophenyl groups, such as are described in EP-A 744397; substituted cinnamoylguanidines, such as are described in EP-A 755919; sulfonimidamides, such as are described in EP-A 771788; benzenedicarbonyldiguanidines, such as are described in EP-A 774458, EP-A 774457; diarylcarbonyldiguanidines, such as are described in EP-A 787717; substituted thiophenylalkenylcarbonylguanidines, such as are described in EP-A 790245; bis-ortho-substituted benzoylguanidines, such as are described in EP-A 8102 07, substituted 1-or 2-naphthylguanidines, such as are described in EP-A 810205 and EP-A 810206; indanylidineacetylguanidines, such as are described in EP-A 837055; phenyl-substituted alkenylcarbonylguanidines, such as are described in EP-A 825178; aminopiperidylbenzoylguanidines, such as are described in EP-A 667341; heterocycloxybenzylguanidines, such as are described in EP-A 694537; ortho-substituted benzoylguanidines, such as are described in EP704431; ortho-substituted alkylbenzylguanidines, such as are described in EP-A 699660; ortho-substituted heterocyclylbenzoylguanidines, such as are described in EP-A 699666; ortho-substituted 5-methylsulfonylbenzoylguanidines, such as are described in EP-A 708088; ortho-substituted 5-alkylsulfonylbenzoylguanidines having 4-amino substituents, such as are described in EP-A 723963; ortho-substituted 5-alkylsulfonylbenzoylguanidines having 4-mercapto substituents, such as are described in EP-A 743301; 4-sulfonyl- or 4-sulfinylbenzylguanidines, such as are described in EP-A 758644; alkenylbenzoylguanidines, such as are described in EP-A 760365; benzoylguanidines with fused, cyclic sulfones, such as are described in DE 19548708; benzoyl-, polycyclic aroyl- and heteroaroylguanidines, such as are described in WO 9426709; 3-aryl/heteroarylbenzoylguanidines, such as are described in WO 9604241; 3-phenylbenzoylguanidines having a basic amide in the 5-position, such as are described in WO 9725310; 3-dihalothienyl- or 3-dihalophenylbenzoylguanidines having a basic substituent in the 5-position, such as are described in WO 9727183; 3-methylsulfonylbenzoylguanidines having specific amino substituents in the 4-position, such as are described in WO 9512584; amiloride derivatives, such as are described in WO 9512592; 3-methylsulfonylbenzoylguanidines having specific amino substituents in the 4-position, such as are described in WO 9726253; indoloylguanidines, such as are described in EP-A 622356 and EP-A 708091; indoloylguanidines having a fused additional ring system, such as are described in EP 787728; methylguanidine derivatives, such as are described in WO 9504052; 1,4-benzoxazinoylguanidines, such as are described in EP-A 719766; 5-bromo-2-naphthoylguanidines, such as are described in JP 8225513; quinoline-4-carbonylguanidines having a phenyl radical in the 2-position, such as are described in EP-A 726254; cinnamoylguanidines, such as are described in JP 09059245; propenoylguanidines having a naphthalene substituent, such as are described JP 9067332; propenoylguanidines having indole substituents, such as are described in JP 9067340; or heteroaryl-substituted acryloylguanidines, such as are described in WO 9711055, and their physiologically tolerable salts.

Preferred NHE inhibitors are the compounds emphasized as preferred in the publications mentioned. Very particularly preferred compounds are cariporide (HOE642), HOE 694, EMD 96785, FR 168888, FR 183998, SM-20550, KBR-9032, and their physiologically tolerable. salts. The most preferred is cariporide or another physiologically tolerable salt of N-(4-isopropyl-3-methanesulfonylbenzoyl) guanidine.

Examples of classes of active compound having cardiovascular activity which can therapeutically be advantageously combined with NCBE inhibitors or can additionally be combined with combinations of NCBE inhibitors and NHE inhibitors are beta-receptor blockers, calcium antagonists, angiotensin-conversion enzyme inhibitors, angiotensin receptor blockers, loop diuretics, thiazide diuretics, potassium-sparing diuretics, aldosterone antagonists, such as are employed, for example, in lowering blood pressure, and also cardiac glycosides or other contractile force-increasing agents in the treatment of cardiac insufficiency and of congestive heart failure, as well as antiarrhythmics of the classes I–IV, nitrates, $K_{ATP}$ openers, $K_{ATP}$ blockers, inhibitors of the veratridine-activatable sodium channel, etc. Thus the following, for example, are suitable: the beta-blockers propanolol, atenolol, metoprolol; the calcium antagonists diltiazem hydrochloride, verapamil hydrochloride, nifedipine; the ACE inhibitors captopril, enalapril, ramipril, trandolapril, quinapril, spirapril, preferably ramipril or trandolapril; the angiotensin II receptor antagonists losartan, valsartan, telmisartan, eprosartan, tasosartan, candesartan, irbesartan; the loop diuretics furosemide, piretanide, torasemide; the thiazide diuretics hydrochlorothiazide, metolazone, indapamide; the potassium-sparing diuretics amiloride, triamterene, spironolactone; the cardiac glycosides digoxin, digitoxin, strophanthin; the antiarrhythmics amiodarone, sotalol, bretylium, flecainide; the nitrate glyceryl trinitrate; the $K^+(ATP)$ openers cromakalim, lemakalim, nocorandil, pinacidil, minoxidil; the inhibitors of the veratridine-activatable $Na^+$ channel.

Blockers of the noninactivating sodium channel (veratridine-activatable sodium channel) are an example of such a particularly advantageous combination component with NCBE inhibitors of the formula I. The combinations of an NCBE inhibitor with a blocker of the noninactivating sodium channel (veratridine-activatable sodium channel) are suitable for infarct and re-infarct prophylaxis and infarct treatment and also for the treatment of angina pectoris and the inhibition of ischemically induced cardiac arrhythmias, tachycardia and the origin and maintenance of ventricular fibrillation, the combinations of an NCBE inhibitor of the formula I with a blocker of the noninactivating sodium channel also inhibiting or greatly decreasing, in a preventive manner, the pathophysiological processes in the formation of ischemically induced damage. Because of their increased protective actions against pathological hypoxic and ischemic situations, the novel combinations of an NCBE inhibitor of the formula I with a blocker of the noninactivating sodium channel can be used, as a result of increased inhibition of the $Na^+$ influx into the cell, as pharmaceuticals for the treatment of all acute or chronic damage caused by ischemia or illnesses primarily or secondarily induced thereby. This relates to their use as pharmaceuticals for surgical interventions, e.g. in organ transplantation, where the combinations of an NCBE inhibitor of the formula I with a blocker of the noninactivating sodium channel can be used both for the protection of the organs in the donor before and during removal, for the protection of removed organs, for example even during storage thereof in physiological bath fluids, and during transfer to the recipient's body. The combinations of an NCBE inhibitor of the formula I with a blocker of the noninactivating sodium channel are also valuable pharmaceuticals having a protective action when carrying out angioplastic surgical interventions, for example on the heart and also on peripheral vessels. Corresponding to their protective action against ischemically induced damage, the combinations of an NCBE inhibitor of the formula I with a blocker of the noninactivating sodium channel are also suitable as pharmaceuticals for the treatment of ischemias of the nervous system, in particular of the central nervous system, where they are suitable for the treatment of stroke or of cerebral edema. Moreover, the novel combinations of an NCBE inhibitor of the formula I with a blocker of the noninactivating sodium channel are also suitable for the treatment of forms of shock, such as, for example, of allergic, cardiogenic, hypovolemic and of bacterial shock.

In addition to administration as a fixed combination, the invention also relates to the simultaneous, separate or sequential administration of NCBE inhibitors of the formula I with NHE inhibitors and/or of an additional active substance from another class of cardiovascular active compounds for the treatment of the abovementioned illnesses.

The invention additionally relates to a pharmaceutical preparation comprising a) an NCBE inhibitor of the formula I and an NHE inhibitor and/or their physiologically tolerable salts; or b) an NCBE inhibitor of the formula I and additionally an active substance from another class of cardiovascular active compound and/or their physiologically tolerable salts; or c) an NCBE inhibitor of the formula I, an NHE inhibitor and additionally an active substance from another class of cardiovascular active compound, and/or their physiologically tolerable salts.

By means of combined administration, the effect of one combination component can be potentiated by the other respective component, i.e. the action and/or duration of action of a novel combination or preparation is stronger or longer lasting than the action and/or duration of action of the respective individual components (synergistic effect). This leads on combined administration to a reduction of the dose of the respective combination component, compared with individual administration. The novel combinations and preparations accordingly have the advantage that the amounts of active compound to be administered can be significantly reduced and undesired side effects can be eliminated or greatly reduced.

The invention furthermore relates to a commercial pack comprising as pharmaceutical active compound a) an NCBE inhibitor of the formula I and an NHE inhibitor and/or their physiologically tolerable salts; or b) an NCBE inhibitor of the formula I and additionally an active substance from another class of cardiovascular active compound and/or their physiologically tolerable salts; or c) an NCBE inhibitor of the formula I, an NHE inhibitor and additionally an active substance from another class of cardiovascular active compound and/or their physiologically tolerable salts, in each case together with instructions for the use of these active compounds in combination for simultaneous, separate or sequential administration in the treatment or prophylaxis of the abovementioned syndromes, in particular for the treatment of cardiovascular disorders.

The pharmaceutical preparations according to the invention can be prepared, for example, by either intensively mixing the individual components as a powder, or by dissolving the individual components in the suitable solvent such as, for example, a lower alcohol and then removing the solvent.

The weight ratio of the NCBE inhibitor to the NHE inhibitor or the substance having cardiovascular activity in the novel combinations and preparations is expediently 1:0.01 to 1:100, preferably 1:0.1 to 1:10.

The novel combinations and preparations in total contain preferably 0.5–99.5% by weight, in particular 4-99% by weight, of these active compounds.

When used according to the invention in mammals, preferably in man, the doses of the various active compound components, for example, vary in the range from 0.001 to 100 mg/kg/day.

List of abbreviations:

| | |
|---|---|
| BCECF | 2',7'-Bis(2-carboxyethyl)-5,6-carboxyfluorescein |
| Bn | Benzyl |
| $CH_2Cl_2$ | Dichloromethane |
| DCI | Desorption Chemical Ionization |
| DIP | Diisopropyl ether |
| DMA | Dimethylacetamide |
| DME | Dimethoxyethane |
| DMF | N,N-Dimethylformamide |
| EA | Ethyl acetate (EtOAc) |
| EI | Electron impact |
| eq | Equivalent |
| ES | Electrospray ionization |
| ESneg | Electrospray, negative ionization |
| Et | Ethyl |
| EtOH | Ethanol |
| FAB | Fast Atom Bombardment |
| Fmoc | 9-Fluorenylmethoxycarbonyl |
| HEP | n-Heptane |
| HOAc | Acetic acid |
| Me | Methyl |
| MeOH | Methanol |
| mp | Melting point |
| MTB | Methyl tertiary-butyl ether |
| NCBE | Sodium-dependent chloride/bicarbonate exchanger |
| NHE | Sodium/hydrogen exchanger |
| NMP | N-Methylpyrrolidone |
| RT | Room temperature |
| THF | Tetrahydrofuran |
| TMU | N,N,N',N'-Tetramethylurea |
| Tol | Toluene |
| CNS | Central nervous system |

EXAMPLES

General Procedure for the Preparation of Sulfonylcyanamides from Sulfonamides

The sulfonamide starting material is dissolved in 10 ml/mmol of anhydrous acetonitrile, 3 mol equivalents of $K_2CO_3$ and one mol equivalent of a 5 N solution of BrCN in acetonitrile are added dropwise and the mixture is heated under reflux until conversion is complete (typical reaction time 10 minutes to 6 hours). The reaction mixture is then chromatographed on silica gel without further working up.

Example 1

Ethyl 2-butyl-5-methylsulfanyl-3-[4-(3'-cyanoaminosulfonylbenzyl)benzyl]-3H-imidazole-4-carboxylate

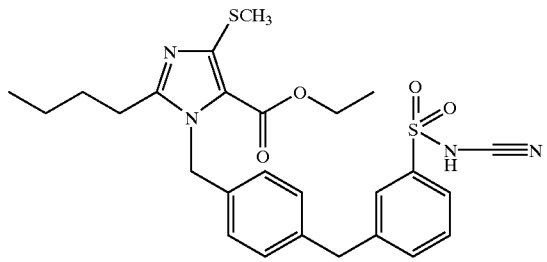

Synthesis Route a) 3-Bromo-N-dimethylaminomethylenebenzenesulfonamide by reaction of 20.3 g of 3-bromobenzenesulfonamide with 57 ml of dimethylformamide dimethyl acetal in 120 ml of DMF at RT for 3 days. After aqueous work-up, the white precipitate is filtered off. The product is dried at 50° C. in vacuo and 20.5 g of colorless solid are obtained, m.p. 122° C., MS (ES): 291 $(M+H)^+$ b) Methyl 4-[3-(dimethylaminomethylenesulfamoyl) benzyl]benzoate by cross-coupling of 3.5 g of 3-bromo-N-dimethylaminomethylenebenzenesulfonamide (1a) with 3 eq of the zinc reagent of methyl 4-bromomethylbenzoate in the presence of 0.1 eq of Pd(II) acetate, 0.2 eq of triphenylphosphine and 0.12 eq of copper(I) iodide in 200 ml of DMF at 80° C. for 3 h. After aqueous work-up, the solvent is removed in vacuo and the residue is chromatographed on silica gel: 4.1 g of colorless solid, m.p. 36–37° C., MS (ES): 361 $(M+H)^+$ c) 4-(3-Sulfamoylbenzyl)benzyl alcohol from 3.0 g of 1b) by reduction with 1.2 g of lithium aluminum hydride in 140 ml of THF at 0° C. for 0.5 h and subsequent refluxing for 2 h. Aqueous work-up yields 1.47 g of colorless solid, m.p. 113–115° C.

d) 4-[3-(Dimethylaminomethylenesulfamoyl)benzyl] benzyl alcohol from 1.7 g of 1c) analogously to reaction procedure 1a), 1.98 g of colorless crystals, m.p. 92° C., MS (ES): 333 $(M+H)^+$ e) Ethyl 2-butyl-5-methylsulfanyl-3-[4-(3-dimethylaminomethylenesulfamoylbenzyl)benzyl]-3H-imidazole-4-carboxylate by nucleophilic substitution of 4-[3-(dimethylaminomethylenesulfamoyl)benzyl]benzyl methanesulfonate prepared in situ [(from 0.7 g of 1d)] by reaction with 1 eq of methanesulfonyl chloride in the presence of 2 eq of triethylamine in methylene chloride at 0° C. for 2 h, subsequent stirring at RT for 1 h and subsequent evaporation of the solvent) with 2 eq of ethyl 2-butyl-5-methylsulfanyl-3H-imidazole-4-carboxylate (J. Med. Chem. 1995, 38, 2357) in the presence of 6 eq of potassium carbonate in 18 ml of DMF at 60° C. for 16 h. Aqueous work-up and subsequent purification by column chromatography yields 0.31 g of colorless oil, MS (ES): 557 $(M+H)^+$ f) Ethyl 2-butyl-5-methylsulfanyl-3-[4-(3-sulfamoylbenzyl)benzyl]-3H-imidazole-4-carboxylate by hydrolysis of 0.3 g of 1e) with 1 ml of semiconc. hydrochloric acid in 1 ml of glacial acetic acid at reflux for 2 h. Addition of water and subsequent drying affords 0.27 g of a colorless resin, MS (ES): 502 $(M+H)^+$ g) Ethyl 2-butyl-5-methylsulfanyl-3-[4-(3'-cyanoaminosulfonylbenzyl)benzyl]-3H-imidazole-4-carboxylate by cyanation of 0.17 g of 1f) analogously to the general procedure yields 0.1 g of colorless solid (resin), m.p. 62° C., MS (ES): 527 $(M+H)^+$.

Example 2

Ethyl 2-butyl-5-methylsulfanyl-3-[3-(3'-cyanoaminosulfonylbenzyl)benzyl]-3H-imidazole-4-carboxylate

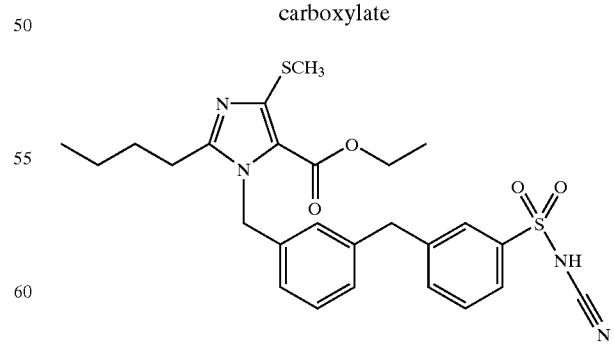

Synthesis Route a) Methyl 3-[3-(dimethylaminomethylenesulfamoyl) benzyl]benzoate by cross-coupling of 3.1 g of 1a) analogously to procedure 1b) starting from 3 eq of methyl 3-bromomethylbenzoate: 3.05 g of colorless solid, m.p. 95° C., MS (ES): 361 (M+H)+ b) 3-(3-Sulfamoylbenzyl)benzyl alcohol from 2.97 g of 2a) by reduction with lithium aluminum hydride analogously to procedure 1c) yields 1.9 g of colorless solid, m.p. 94° C., MS (Cl): 277 (M)+ c) 3-[3-(Dimethylaminomethylenesulfamoyl)benzyl] benzyl alcohol from 1.39 g of 2b) analogously to reaction procedure 1a), 1.41 g of colorless crystals, m.p. 99–100° C., MS (ES): 333 (M+H)+ d) Ethyl 2-butyl-5-methylsulfanyl-3-[3-(3-dimethylaminomethylenesulfamoylbenzyl)benzyl]-3H-imidazole-4-carboxylate by nucleophilic substitution of 3-[3-(dimethylaminomethylenesulfamoyl)benzyl]benzyl methanesulfonate prepared in situ [(from 0.28 g of 2c)] analogously to procedure 1), 0.15 g of colorless resin, MS (ES): 557 (M+H)+ e) Ethyl 2-butyl-5-methylsulfanyl-3-[3-(3-sulfamoylbenzyl)benzyl]-3H-imidazole-4-carboxylate by hydrolysis of 0.15 g of 2d) analogously to procedure 1f) affords 0.13 g of colorless crystals, m.p. 49° C., MS (ES): 502 (M+H)+ f) Ethyl 2-butyl-5-methylsulfanyl-3-[3-(3'-cyanoaminosulfonylbenzyl)benzyl]-3H-imidazole-4-carboxylate by cyanation of 0.12 g of 2e) analogously to the general procedure yields 0.07 g of colorless solid (resin), m.p. 172–174° C., MS (ES): 527 (M+H)+

Example 3

2-Phenyl-4-formyl-5-chloro-3-[3-(3'-cyanoaminosulfonylbenzyl)benzyl]-3H-imidazole

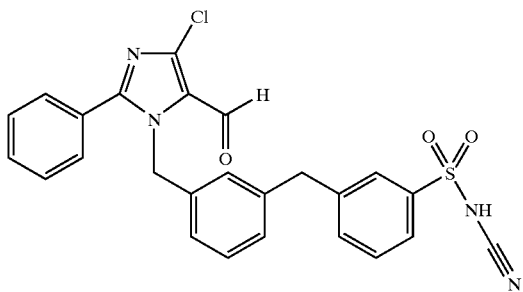

Synthesis Route a) 2-Phenyl-4-formyl-5-chloro-3-[3-(3-dimethylaminomethylenesulfamoylbenzyl)benzyl]-3H-imidazole by nucleophilic substitution of 3-[3-dimethylaminomethylenesulfamoyl)benzyl]benzyl methanesulfonate prepared in situ [(from 0.58 g of 2c)] analogously to procedure 1e), but using 0.72 g of 5-chloro-4-formyl-2-phenyl-3H-imidazole (Chem. Pharm. Bull. 1976, 24(5), 960), 0.19 g of colorless oil, MS (ES): 521 (M+H)+ b) 2-Phenyl-4-formyl-5-chloro-3-[3-(3-sulfamoylbenzyl)benzyl]-3H-imidazole by hydrolysis of 0.17 g of 2a) analogously to procedure 1f) affords 0.13 g of colorless crystals, m.p. 83–85° C., MS (ES): 466 (M+H)+ c) 2-Phenyl-4-formyl-5-chloro-3-[3-(3'-cyanoaminosulfonylbenzyl)benzyl]-3H-imidazole by cyanation of 0.13 g of 3b) analogously to the general procedure yields 0.08 g of colorless solid, m.p. 75° C., MS (ES): 491 (M+H)+

Example 4

2-[4-(4-Chloro-5-formyl-2-phenylimidazol-1-ylmethyl)benzenesulfonyl]benzenesulfonyl cyanamide

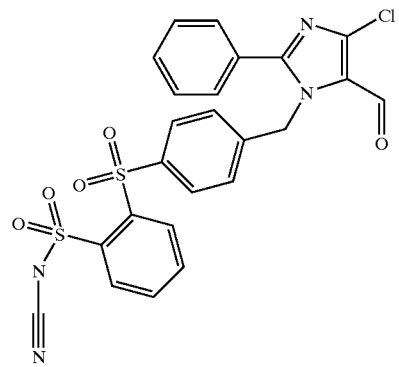

a) 2-p-Tolylsulfanylbenzenesulfonamide 3.0 g of 2-chlorobenzenesulfonamide, 2.0 g of thiocresol and 6.5 g of K$_2$CO$_3$ are stirred at 100° C. for 6 h in 30 ml of DMF and then at 120° C. for 13 h. The reaction mixture is poured onto 200 ml of water and extracted with 500 ml of EA. The organic phase is then washed with 100 ml of a saturated aqueous Na$_2$CO$_3$ solution. It is dried over MgSO$_4$ and the solvent is removed in vacuo. Chromatography on silica gel using DIP yields 1.4 g of white crystals, m.p. 122–124° C.

R$_f$(DIP)=0.36 MS (ES): 280 (M+H)+ b) N-Dimethylaminomethylene-2-p-tolyisuffanylbenzenesulfonamide 1.4 g of 2-p-tolylsulfanylbenzenesulfonamide are stirred at RT for 2 h in 10 ml of dimethoxymethyldimethylamine. The reaction mixture is then poured onto 500 ml of water, subsequently stirred for 2 h and the product is filtered off with suction and dried in vacuo. 1.6 g of white crystals are obtained, m.p. 151° C.

R$_f$(MTB)=0.28 MS (DCI): 335 (M+H)+ c) N-Dimethylaminomethylene-2-(toluene-4-sulfonyl)benzenesulfonamide 1.5 g of N-dimethylaminomethylene-2-p-tolylsulfanylbenzenesulfonamide are dissolved in 50 ml of CH$_2$Cl$_2$ and treated with 2.6 g of m-chloroperbenzoic acid at 0° C. The mixture is subsequently stirred at RT for 3 h, then treated with 100 ml of a saturated aqueous Na$_2$SO$_3$ solution and stirred at RT for a further 5 minutes. It is diluted with 150 ml of CH$_2$Cl$_2$ and washed 2 times with 50 ml of a saturated aqueous Na$_2$CO$_3$ solution each time. It is dried over MgSO$_4$ and the solvent is removed in vacuo. 1.5 g of white crystals are obtained, m.p. 178° C.

R$_f$(EA)=0.44 MS (ES): 367 (M+H)+ d) 2-(4-Bromomethylbenzenesulfonyl)-N-dimethylaminomethylenebenzenesulfonamide 1.5 g of N-dimethylaminomethylene-2-(toluene-4-sulfonyl)benzenesulfonamide, 0.74 g of NBS and 20 mg of benzoyl peroxide are refluxed for 2 h in 15 ml of chlorobenzene. The reaction mixture is allowed to cool and is diluted with 100 ml of toluene, and washed once each with 20 ml of a saturated aqueous Na$_2$SO$_3$ solution and twice with 50 ml of a saturated aqueous Na$_2$CO$_3$ solution. It is dried over MgSO$_4$ and the solvent is removed in vacuo. 1.6 g of an amorphous solid are obtained, which is further reacted without further purification.

R$_f$(EA)=0.44 MS (ES): 445 (M+H)$^+$ e) 2-[4-(4-Chloro-5-formyl-2-phenylimidazol-1-ylmethyl)benzenesulfonyl]-N-dimethylaminomethylenebenzenesulfonamide 1.6 g of 2-(4-bromomethylbenzenesulfonyl)-N-dimethylaminomethylenebenzenesulfonamide, 680 mg of 5-chloro-2-phenyl-3H-imidazole-4-carbaldehyde and 1.4 g of K$_2$CO$_3$ are stirred at RT for 3 days in 15 ml of anhydrous DMF. The reaction mixture is then diluted with 200 ml of EA and washed three times with 50 ml of a saturated aqueous Na$_2$CO$_3$ solution each time. It is dried over MgSO$_4$ and the solvent is removed in vacuo. Chromatography on silica gel using MTB yields 240 mg of a colorless oil.

R$_f$(MTB)=0.08 MS (ES): 571 (M+H)$^+$ f) 2-[4-(4-Chloro-5-formyl-2-phenylimidazol-1-ylmethyl)benzenesulfonyl]benzenesulfonamide 230 mg of 2-[4-(4-chloro-5-formyl-2-phenylimidazol-1-ylmethyl)benzenesulfonyl]-N-dimethylaminomethylenebenzenesulfonamide are refluxed for 2 h in 3 ml of EtOH and 3 ml of a saturated aqueous HCl solution. The reaction mixture is allowed to cool and poured onto 10 ml of water, and the product is filtered off. Chromatography on silica gel using MTB yields 151 mg of an amorphous solid.

Rf(MTB)=0.41 MS (ES): 516 (M+H)$^+$ g) 2-[4-(4-Chloro-5-formyl-2-phenylimidazol-1-ylmethyl)benzenesulfonyl]benzenesulfonyl cyanamide 145 mg of 2-[4-(4-chloro-5-formyl-2-phenylimidazol-1-ylmethyl)benzenesulfonyl]benzenesulfonamide, 117 mg of K$_2$CO$_3$ and 56 µl of a 5 M solution of BrCN in acetonitrile are refluxed for 90 minutes in 2 ml of anhydrous acetonitrile. The reaction mixture is allowed to cool, is chromatographed using EA/MeOH 10:1 and 90 mg of an amorphous solid are obtained.

R$_f$(EA/MeOH 10:1)=0.27 MS (ES): 541 (M+H)$^+$

Pharmacological Data

Inhibition of the Na$^+$-dependent Cl$^-$/HCO$_3$ exchanger (NCBE) in human endothelial cells Human endothelial cells (ECV-304) were detached from culture flasks with the aid of trypsin/EDTA buffer (0.05/0.02% in phosphate buffer) and, after centrifugation (100 g, 5 min), taken up in a buffered salt solution (mmol/l: 115 NaCl, 20 NH$_4$Cl, 5 KCl, 1 CaCl$_2$, 1 MgSO$_4$, 20 N-(2-hydroxyethyl)piperazine-N=-2-ethanesulfonic acid (HEPES), 5 glucose and 1, g/l of bovine serum albumin; pH 7.4). This cell suspension was incubated at 37° C. for 20 min with 5 µM BCECF acetoxymethyl ester. The cells were then washed and resuspended in a sodium- and bicarbonate-free buffer solution (mmol/l: 5 HEPES, 133.8 choline chloride, 4.7 KCl, 1.25 MgCl$_2$, 0.97 K$_2$HPO$_4$, 0.23 KH$_2$PO$_4$, 5 glucose; pH 7.4).

For the subsequent fluorescence measurement in the FLIPR (Fluorescent Imaging Plate Reader), 100 µl of this cell suspension in each case containing 20,000 cells were added by pipette per well of a 96-well microtiter plate and this microtiter plate was centrifuged (100 g, 5 min). In the FLIPR, 100 µl of buffer solution in each case were then removed from a further prepared microtiter plate and added by pipette to each of the 96 wells of the measuring plate. In this case, for a 100% control, i.e. a recovery of the intracellular pH (pH$_i$) by means of the NCBE, a bicarbonate- and sodium-containing buffer solution (mmol/l: 5 HEPES, 93.8 NaCl, 40 NaHCO$_3$, 4.7 KCl, 1.25 CaCl$_2$, 1.25 MgCl$_2$, 0.97 Na$_2$HPO$_4$, 0.23 NaH$_2$PO$_4$, 5 glucose; pH 7.4) which contained 50 µM HOE 642 was used. For a 0% control, i.e. no pHi recovery at all, a bicarbonate-free, sodium-containing buffer solution (mmol/l: 5 HEPES, 133.8 NaCl, 4.7 KCl, 1.25 CaCl$_2$, 1.25 MgCl$_2$, 0.97 Na$_2$HPO$_4$, 0.23 NaH$_2$PO$_4$, 5 glucose; pH 7.4) to which 50 µM HOE 642 were also added was employed. The compounds of the formula (I) according to the invention were added in various concentrations of the sodium- and bicarbonate-containing solution.

After addition of the buffer solutions to the dye-loaded acidified cells situated in the measuring plate, the increase in the fluorescence intensity which corresponded to an increase in the pH$_i$ was determined in each well of the microtiter plate. The kinetics were in this case recorded at 35° C. over a period of 2 minutes.

The increase in the fluorescence intensities for different concentrations of the compounds according to the invention was related to the two controls and from this the inhibitory action of the substances was determined.

Results

Residual activity of the NCBE at an inhibitor concentration of 10 µM

| Example | Residual activity in % |
|---------|------------------------|
| 1 | 11.1 |
| 2 | 35.2 |
| 3 | 24.3 |

We claim:

1. A compound of the formula (I) or a physiologically tolerable salt of formula (I), wherein formula (I) is

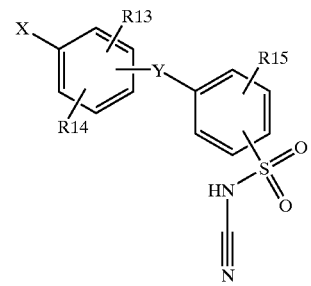

in which the symbols have the following meanings:
X is equal to

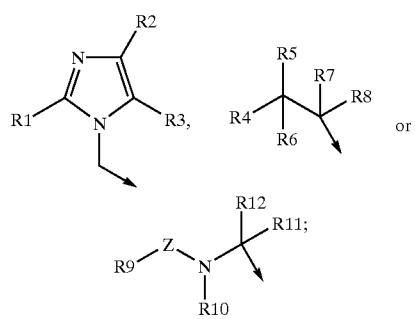

R(1) is hydrogen, alkyl having 1, 2, 3, 4, 5, 6, 7 or 8 carbon atoms; or —C$_a$H$_{2a}$-phenyl, where the phenyl moiety is unsubstituted or substituted by 1, 2 or 3 identical or different radicals from F, Cl, Br, I, CF$_3$, methyl, methoxy, hydroxy or NR(19)R(20);

R(19) and R(20) independently of one another are H or alkyl having 1, 2, 3 or 4 carbon atoms;

a is zero, 1 or 2; or

R(1) is —$C_bH_{2b}$-heteroaryl having 1, 2, 3, 4, 5, 6, 7, 8 or 9 carbon atoms where the heteroaryl moiety is unsubstituted or substituted by 1, 2 or 3 identical or different radicals from F, Cl, Br, I, $CF_3$, $CH_3$, methoxy, hydroxy or NR(21)R(22);

R(21) and R(22) independently of one another are H or alkyl having 1, 2, 3 or 4 carbon atoms;

b is zero, 1 or 2; or

R(1) is —$C_cH_{2c}$-cycloalkyl having 3, 4, 5, 6 or 7 carbon atoms;

c is zero, 1 or 2;

R(2) and R(3) independently of one another are hydrogen, F, Cl, Br, I, $CF_3$, —CN, —$NO_2$, $CH_2OR(23)$, CO—R(24) or O—R(25);

R(23) is hydrogen or alkyl having 1, 2, 3, 4, 5, 6, 7 or 8 carbon atoms;

R(24) is hydrogen, alkyl having 1, 2, 3, 4, 5, 6, 7 or 8 carbon atoms, OR(26) or phenyl;

where phenyl is unsubstituted or substituted by 1, 2 or 3 identical or different radicals from F, Cl, Br, I, $CF_3$, methyl, methoxy, hydroxy or NR(27)R(28);

R(27) and R(28) independently of one another are H or alkyl having 1, 2, 3 or 4 carbon atoms;

R(26) is hydrogen or alkyl having 1, 2, 3, 4, 5, 6, 7 or 8 carbon atoms;

R(25) is hydrogen, alkyl having 1, 2, 3, 4, 5, 6, 7 or 8 carbon atoms, or phenyl;

where phenyl is unsubstituted or substituted by 1, 2 or 3 identical or different radicals from F, Cl, Br, I, $CF_3$, methyl, methoxy, hydroxy or NR(29)R(30);

R(29) and R(30) independently of one another are H or alkyl having 1, 2, 3 or 4 carbon atoms; or R(25) is heteroaryl having 1, 2, 3, 4, 5, 6, 7, 8 or 9 carbon atoms, which is unsubstituted or substituted by 1, 2 or 3 identical or different radicals from F, Cl, Br, I, $CF_3$, $CH_3$, methoxy, hydroxy or NR(31)R(32);

R(31) and R(32) independently of one another are H or alkyl having 1, 2, 3 or 4 carbon atoms; or R(2) and R(3) independently of one another are alkyl having 1, 2, 3, 4, 5, 6, 7 or 8 carbon atoms, cycloalkyl having 3, 4, 5, 6 or 7 carbon atoms; or —$C_dH_{2d}$-phenyl, where the phenyl moiety is unsubstituted or substituted by 1, 2 or 3 identical or different radicals from F, Cl, Br, I, $CF_3$, methyl, methoxy, hydroxy or NR(33)R(34);

R(33) and R(34) independently of one another are H or alkyl having 1, 2, 3 or 4 carbon atoms;

d is zero, 1 or 2; or

R(2) and R(3) independently of one another are

—$C_eH_{2e}$-heteroaryl having 1, 2, 3, 4, 5, 6, 7, 8 or 9 carbon atoms, where the heteroaryl moiety is unsubstituted or substituted by 1, 2 or 3 identical or different radicals from F, Cl, Br, I, $CF_3$, $CH_3$, methoxy, hydroxy or NR(35)R(36);

R(35) and R(36) independently of one another are H or alkyl having 1, 2, 3 or 4 carbon atoms;

e is zero, 1 or 2; or

R(2) and R(3) independently of one another are

—$SO_f$—R(37);

R(37) is alkyl having 1, 2, 3, 4, 5, 6, 7 or 8 carbon atoms, cycloalkyl having 3, 4, 5, 6 or 7 carbon atoms, or —$C_gH_{2g}$-phenyl, where the phenyl moiety is unsubstituted or substituted by 1, 2 or 3 identical or different radicals from F, Cl, Br, I, $CF_3$, methyl, methoxy, hydroxy or NR(38)R(39);

R(38) and R(39) independently of one another are H or alkyl having 1, 2, 3 or 4 carbon atoms;

f is zero, 1 or 2;

g is zero, 1 or 2;

R(4) is hydrogen, alkyl having 1, 2, 3, 4, 5, 6, 7 or 8 carbon atoms, 1-naphthyl, 2-naphthyl, —$C_iH_{2i}$-cycloalkyl having 3, 4, 5, 6 or 7 carbon atoms or —$C_iH_{2i}$-phenyl, where the phenyl moiety is unsubstituted or substituted by 1, 2 or 3 identical or different radicals from alkyl having 1, 2, 3, 4, 5, 6, 7 or 8 carbon atoms, F, Cl, Br, I, $CF_3$, $SO_jR(48)$, OR(49), NR(50)R(51), —CN, —$NO_2$ or CO—R(52);

i is zero, 1 or 2;

R(48) is alkyl having 1, 2, 3 or 4 carbon atoms or NR(53)R(54);

R(53) and R(54) independently of one another are hydrogen or alkyl having 1, 2, 3 or 4 carbon atoms;

j is zero, 1 or 2;

R(49) is hydrogen or alkyl having 1, 2, 3 or 4 carbon atoms;

R(50) and R(51) independently of one another are hydrogen or alkyl having 1, 2, 3 or 4 carbon atoms;

R(52) is hydrogen or alkyl having 1, 2, 3, 4, 5, 6, 7 or 8 carbon atoms or OR(55);

R(55) is hydrogen or alkyl having 1, 2, 3, 4, 5, 6, 7, or 8 carbon atoms; or

R(4) and R(6) together with the carbon atom carrying them are cycloalkyl having 3, 4, 5, 6 or 7 carbon atoms or fluorenyl;

R(5), R(6), R(7) and R(8) independently of one another are hydrogen, F, $CF_3$, O—R(56), alkyl having 1, 2, 3, 4, 5, 6, 7 or 8 carbon atoms, cycloalkyl having 3, 4, 5, 6 or 7 carbon atoms, —$C_kH_{2k}$-phenyl, where the phenyl moiety is unsubstituted or substituted by 1, 2 or 3 identical or different radicals from F, Cl, Br, I, $CF_3$, methyl, methoxy, hydroxy or NR(57)R(58);

R(57) and R(58) independently of one another are hydrogen or alkyl having 1, 2, 3 or 4 carbon atoms;

k is zero, 1 or 2;

R(56) is hydrogen, alkyl having 1, 2, 3, 4, 5, 6, 7 or 8 carbon atoms, or phenyl, which is unsubstituted or substituted by 1, 2 or 3 identical or different radicals from F, Cl, Br, I, $CF_3$, methyl, methoxy, hydroxy or NR(59)R(60);

R(59) and R(60) independently of one another are hydrogen or alkyl having 1, 2, 3 or 4 carbon atoms, R(56) is heteroaryl having 1, 2, 3, 4, 5, 6, 7, 8 or 9 carbon atoms, which is unsubstituted or substituted by 1, 2 or 3 identical or different radicals from F, Cl, Br, I, $CF_3$, $CH_3$, methoxy, hydroxy or NR(61)R(62);

R(61) and R(62) independently of one another are hydrogen or alkyl having 1, 2, 3 or 4 carbon atoms; or R(5) and R(7) together are a second bond between the carbon atoms carrying the radicals R(6) and R(8), where R(4), R(6) and R(8) are as defined above;

R(9) is alkyl having 1, 2, 3, 4, 5, 6, 7 or 8 carbon atoms, alkenyl having 2, 3, 4, 5, 6, 7 or 8 carbon atoms, or —$C_lH_{2l-ll}$—A;

ll is zero or 2; and

I is zero, 1, 2, 3 or 4;
  where I is unequal to zero or 1, when II is equal to 2;
R(10) is hydrogen;
  alkyl having 1, 2, 3, 4, 5, 6, 7 or 8 carbon atoms;
  alkenyl having 2, 3, 4, 5, 6, 7 or 8 carbon atoms; or —$C_mH_{2m-mm}$—B,
  mm is zero or 2; and
  m is zero, 1,2,3 or 4;
    where m is unequal to zero or 1, when mm is equal to 2;
R(11) and R(12) independently of one another are hydrogen or alkyl having 1, 2, 3, 4, 5, 6, 7 or 8 carbon atoms;
Z is carbonyl or sulfonyl;
A and B independently of one another are
  1. aryl having 6, 7, 8, 9, 10, 11, 12, 13 or 14 carbon atoms;
  2. a radical as defined in 1, substituted by 1, 2 or 3 identical or different radicals from alkyl having 1, 2, 3, 4, 5, 6, 7 or 8 carbon atoms, F, Cl, Br, I, $CF_3$, $SO_nR(63)$, OR(64), NR(65)R(66), —CN, —$NO_2$ or CO—R(67);
  3. heteroaryl having 1, 2, 3, 4, 5, 6, 7, 8 or 9 carbon atoms;
  4. a radical as defined in 3, substituted by 1, 2 or 3 identical or different radicals from F, Cl, Br, I, $CF_3$, $CH_3$, methoxy, hydroxy or NR(68)R(69);
  5. cycloalkyl having 3, 4, 5, 6 or 7 carbon atoms;
  6. O—R(70); or
  7. O—R(71);
n is zero, 1 or 2;
R(70) and R(71) independently of one another are
  1. hydrogen;
  2. alkyl having 1, 2, 3, 4, 5, 6, 7 or 8 carbon atoms;
  3. —$C_oH_{2o-oo}$-phenyl,
    oo is zero or 2; and
    o is zero, 1, 2, 3 or 4;
    where o is unequal to zero or 1, when oo is equal to 2;
  4. a radical as defined in 3, where the phenyl moiety is substituted by 1, 2 or 3 identical or different radicals from alkyl having 1, 2, 3, 4, 5, 6, 7 or 8 carbon atoms, F, Cl, Br, I, $CF_3$, $SO_pR(72)$, OR(73), NR(74)R(75), —CN, —$NO_2$ or CO—R(76); or
  5. alkenyl having 2, 3, 4, 5, 6, 7 or 8 carbon atoms;
    R(63) and R(72) independently of one another are alkyl having 1, 2, 3 or 4 carbon atoms or NR(77)R(78);
    R(67) and R(76) independently of one another are hydrogen, alkyl having 1, 2, 3, 4, 5, 6, 7 or 8 carbon atoms or OR(89);
    R(89) is hydrogen or alkyl having 1, 2, 3, 4, 5, 6, 7 or 8 carbon atoms;
    R(64), R(65), R(66), R(68), R(69), R(73), R(74), R(75), R(77) and R(78) independently of one another are hydrogen or alkyl having 1, 2, 3 or 4 carbon atoms;
  p is zero, 1 or 2;
R(13), R(14) and R(15) independently of one another are hydrogen, alkyl having 1, 2, 3, 4, 5, 6, 7 or 8 carbon atoms, F, Cl, Br, I, $CF_3$, —CN, —$NO_2$, $SO_q$—R(79), CO—R(80) or O—R(81);
q is zero, 1, or 2;
R(79) is alkyl having 1, 2, 3, 4, 5, 6, 7 or 8 carbon atoms or phenyl, which is unsubstituted or substituted by 1, 2 or 3 identical or different radicals from F, Cl, Br, I, $CF_3$, methyl, methoxy, hydroxy or NR(82)R(83);
  R(82), R(83) independently of one another are hydrogen or alkyl having 1, 2, 3 or 4 carbon atoms;
R(80) is hydrogen, alkyl having 1, 2, 3, 4, 5, 6, 7 or 8 carbon atoms or OR(84);
  R(84) is hydrogen or alkyl having 1, 2, 3, 4, 5, 6, 7 or 8 carbon atoms;
R(81) is hydrogen, alkyl having 1, 2, 3, 4, 5, 6, 7 or 8 carbon atoms or phenyl, which is unsubstituted or substituted by 1, 2 or 3 identical or different radicals from F, Cl, Br, I, $CF_3$, methyl, methoxy, hydroxy or NR(82)R(83);
Y is CR(16)R(17), CO, S, $SO_2$, O, or NR(18),
R(16) is hydrogen or —OR(85);
  R(85) is hydrogen, alkyl having 1, 2, 3, 4, 5, 6, 7 or 8 carbon atoms or CO—R(86);
  R(86) is alkyl having 1, 2, 3, 4, 5, 6, 7 or 8 carbon atoms or phenyl, which is unsubstituted or substituted by 1, 2 or 3 identical or different radicals from F, Cl, Br, I, $CF_3$, methyl, methoxy or hydroxyl;
R(17) is hydrogen or alkyl having 1, 2, 3, 4, 5, 6, 7 or 8 carbon atoms;
R(18) is hydrogen, alkyl having 1, 2, 3, 4, 5, 6, 7 or 8 carbon atoms, CO—R(87) or $SO_2R(88)$;
  R(87) and R(88) independently of one another are alkyl having 1, 2, 3, 4, 5, 6, 7 or 8 carbon atoms, cycloalkyl having 3, 4, 5, 6, 7 or 8 carbon atoms or phenyl, which is unsubstituted or substituted by 1, 2 or 3 identical or different radicals from F, Cl, Br, I, $CF_3$, methyl, methoxy or hydroxyl.

2. A compound as claimed in claim 1, in which:
X is equal to

R(1) is hydrogen, alkyl having 1, 2, 3 or 4 carbon atoms or —$C_aH_{2a}$-phenyl, where the phenyl moiety is unsubstituted or substituted by 1, 2 or 3 identical or different radicals from F, Cl, Br, I, $CF_3$, methyl, methoxy or hydroxyl;
  a is zero or 1; or
R(1) is heteroaryl having 1, 2, 3, 4, 5, 6, 7, 8 or 9 carbon atoms, which is unsubstituted or substituted by 1, 2 or 3 identical or different radicals from F, Cl, Br, I, $CF_3$, $CH_3$, methoxy or hydroxyl; or
R(1) is —$C_cH_{2c}$-cycloalkyl having 3, 4, 5, 6 or 7 carbon atoms;
  c is zero or 1;
R(2) and R(3) independently of one another are hydrogen, F, Cl, Br, I, $CF_3$, —CN, —$NO_2$, $CH_2OR(23)$, CO—R(24) or O—R(25);
  R(23) is hydrogen or alkyl having 1, 2, 3 or 4 carbon atoms;

R(24) is hydrogen, alkyl having 1, 2, 3 or 4 carbon atoms, OR(26) or phenyl, which is unsubstituted or substituted by 1, 2 or 3 identical or different radicals from F, Cl, Br, I, $CF_3$, methyl, methoxy or hydroxyl;

R(26) is hydrogen or alkyl having 1, 2, 3 or 4 carbon atoms;

R(25) is hydrogen, alkyl having 1, 2, 3 or 4 carbon atoms, or phenyl, which is unsubstituted or substituted by 1, 2 or 3 identical or different radicals from F, Cl, Br, I, $CF_3$, methyl, methoxy or hydroxyl; or R(25) is heteroaryl having 1, 2, 3, 4, 5, 6, 7, 8 or 9 carbon atoms, which is unsubstituted or substituted by 1, 2 or 3 identical or different radicals from F, Cl, Br, I, $CF_3$, $CH_3$, or methoxy; or R(2) and R(3) independently of one another are alkyl having 1, 2, 3 or 4 carbon atoms, cycloalkyl having 3, 4, 5, 6 or 7 carbon atoms, or —$C_dH_{2d}$-phenyl, where the phenyl moiety is unsubstituted or substituted by 1, 2 or 3 identical or different radicals from F, Cl, Br, I, $CF_3$, methyl, methoxy or hydroxyl;

d is zero or 1; or

R(2) and R(3) independently of one another are heteroaryl having 1, 2, 3, 4, 5, 6, 7, 8 or 9 carbon atoms, which is unsubstituted or substituted by 1, 2 or 3 identical or different radicals from F, Cl, Br, I, $CF_3$, $CH_3$, methoxy or hydroxyl; or R(2) and R(3) independently of one another are
—$SO_f$—R(37);

R(37) is alkyl having 1, 2, 3 or 4 carbon atoms, cycloalkyl having 3, 4, 5, 6 or 7 carbon atoms, or —$C_gH_{2g}$-phenyl, where the phenyl moiety is unsubstituted or substituted by 1, 2 or 3 identical or different radicals from F, Cl, Br, I, $CF_3$, methyl, methoxy or hydroxyl;

f is zero, 1 or 2;
g is zero or 1;

R(4) is hydrogen, alkyl having 1, 2, 3 or 4 carbon atoms, 1-naphthyl, 2-naphthyl, —$C_iH_{2i}$-cycloalkyl having 3, 4, 5, 6 or 7 carbon atoms or —$C_iH_{2i}$-phenyl, where the phenyl moiety is unsubstituted or substituted by 1, 2 or 3 identical or different radicals from alkyl having 1, 2, 3, 4, 5, 6, 7 or 8 carbon atoms, F, Cl, $CF_3$, $SO_jR(48)$, OR(49), NR(50)R(51), —CN or CO—R(52);

i is zero, 1 or 2;

R(48) is alkyl having 1, 2, 3 or 4 carbon atoms or NR(53)R(54),

R(53) and R(54) independently of one another are hydrogen, methyl or ethyl;

j is zero or 2;

R(49) is hydrogen or alkyl having 1, 2, 3 or 4 carbon atoms;

R(50) and R(51) independently of one another are hydrogen, methyl or ethyl;

R(52) is hydrogen, alkyl having 1, 2, 3 or 4 carbon atoms or OR(55);

R(55) is hydrogen or alkyl having 1, 2, 3 or 4 carbon atoms; or

R(4) and R(6) together with the carbon atom carrying them are cycloalkyl having 3, 4, 5, 6 or 7 carbon atoms or fluorenyl;

R(5), R(6), R(7) and R(8) independently of one another are hydrogen, F, $CF_3$, O—R(56), alkyl having 1, 2, 3 or 4 carbon atoms, cycloalkyl having 3, 4, 5, 6 or 7 carbon atoms, or —$C_kH_{2k}$-phenyl, where the phenyl moiety is unsubstituted or substituted by 1, 2 or 3 identical or different radicals from F, Cl, Br, I, $CF_3$, methyl, methoxy or hydroxyl;

k is zero or 1;

R(56) is hydrogen, alkyl having 1, 2, 3 or 4 carbon atoms, or phenyl, which is unsubstituted or substituted by 1, 2 or 3 identical or different radicals from F, Cl, Br, I, $CF_3$, methyl, methoxy or hydroxyl; or R(56) is heteroaryl having 1, 2, 3, 4, 5, 6, 7, 8 or 9 carbon atoms, which is unsubstituted or substituted by 1, 2 or 3 identical or different radicals from F, Cl, Br, I, $CF_3$, $CH_3$, methoxy or hydroxyl; or R(5) and R(7) together are a second bond between the carbon atoms carrying the radicals R(6) and R(8), where R(4), R(6), R(8) are as defined above;

R(9)
is alkyl having 1, 2, 3 or 4 carbon atoms, alkenyl having 2, 3 or 4 carbon atoms; or —$C_IH_{2I-II}$—A;
II is zero or 2; and
I is zero, 1, 2 or 3;
where I is unequal to zero or 1, when II is equal to 2;

R(10) is hydrogen;
alkyl having 1, 2, 3 or 4 carbon atoms;
alkenyl having 2, 3 or 4 carbon atoms; or —$C_mH_{2m-mm}$—B,
mm is zero or 2; and
m is zero, 1, 2 or 3;
where m is unequal to zero or 1, when mm is equal to 2;

R(11) and R(12) independently of one another are hydrogen or alkyl having 1, 2, 3 or 4 carbon atoms;

Z is carbonyl or sulfonyl;

A and B independently of one another are
1. phenyl;
2. a radical as defined in 1, substituted by 1, 2, or 3 identical or different radicals from alkyl having 1, 2, 3 or 4 carbon atoms, F, Cl, $CF_3$, $SO_nR(63)$, OR(64), —CN or CO—R(67);
3. 1-naphthyl or 2-naphthyl;
4. a radical as defined in 3, substituted by 1, 2 or 3 identical or different radicals from alkyl having 1, 2, 3 or 4 carbon atoms, F, Cl, $CF_3$, $CH_3$, methoxy or hydroxyl;
5. heteroaryl having 1, 2, 3, 4, 5, 6, 7, 8 or 9 carbon atoms;
6. a radical as defined in 5, substituted by 1, 2 or 3 identical or different radicals from alkyl having 1 2, 3 or 4 carbon atoms F, Cl, $CF_3$, $CH_3$, methoxy or hydroxyl;
7. cycloalkyl having 3, 4, 5, 6 or 7 carbon atoms;
8. O—R(70); or
9. O—R(71);
n is zero, one or two;
R(70) and R(71) independently of one another are
1. hydrogen;
2. alkyl having 1, 2, 3 or 4 carbon atoms;
3. —$C_oH_{2o-oo}$-phenyl,
oo is zero or 2; and
o is zero, 1,2 or 3;
where o is unequal to zero or 1, when oo is equal to 2;
4. a radical as defined in 3, where the phenyl moiety is substituted by 1, 2 or 3 identical or different radicals from alkyl having 1, 2, 3 or 4 carbon atoms, F, Cl, $CF_3$, $SO_pR(72)$, OR(73), —CN, —$NO_2$ or CO—R (76); or 5. alkenyl having 2, 3 or 4 carbon atoms;
   R(63) and R(72) independently of one another are alkyl having 1, 2, 3 or 4 carbon atoms or NR(77)R(78) as defined in claim 1;
   R(67) and R(76) independently of one another are alkyl having 1, 2, 3 or 4 carbon atoms or O-alkyl having 1, 2, 3 or 4 carbon atoms;
   R(64) and R(73) independently of one another are hydrogen or alkyl having 1, 2, 3 or 4 carbon atoms;
   p is zero, 1 or 2;
R(13), R(14) and R(15) independently of one another are hydrogen, alkyl having 1, 2, 3 or 4 carbon atoms, F, Cl, CF$_3$, —CN, SO$_q$—R(79), CO—R(80) or O—R(81);
q is zero, 1 or 2;
   R(79) is alkyl having 1, 2, 3 or 4 carbon atoms or phenyl, which is unsubstituted or substituted by 1, 2 or 3 identical or different radicals from F, Cl, CF$_3$, methyl, methoxy or hydroxyl;
   R(80) is hydrogen, alkyl having 1, 2, 3 or 4 carbon atoms or OR(84); R(84) is hydrogen or alkyl having 1, 2, 3 or 4 carbon atoms;
   R(81) is hydrogen, alkyl having 1, 2, 3 or 4 carbon atoms or phenyl, which is unsubstituted or substituted by 1, 2 or 3 identical or different radicals from F, Cl, CF$_3$, methyl, methoxy or hydroxyl;
Y is CR(16) R(17), CO, S, SO$_2$, O or NR(18);
   R(16) is hydrogen or —OR(85);
      R(85) is hydrogen or alkyl having 1, 2, 3 or 4 carbon atoms or COR(86);
      R(86) is alkyl having 1, 2, 3 or 4 carbon atoms or phenyl, which is unsubstituted or substituted by 1, 2 or 3 identical or different radicals from F, Cl, CF$_3$, methyl or methoxy;
   R(17) is hydrogen or alkyl having 1, 2, 3 or 4 carbon atoms;
   R(18) is hydrogen or alkyl having 1, 2, 3 or 4 carbon atoms, COR(87) or SO$_2$R(88);
R(87) and R(88) independently of one another are alkyl having 1, 2, 3 or 4 carbon atoms, cycloalkyl having 3, 4, 5, 6, 7 or 8 carbon atoms or phenyl, which is unsubstituted or substituted by 1, 2 or 3 identical or different radicals from F, Cl, Br, I, CF$_3$, methyl or methoxy.

3. A compound as claimed in claim 1, in which:
X is

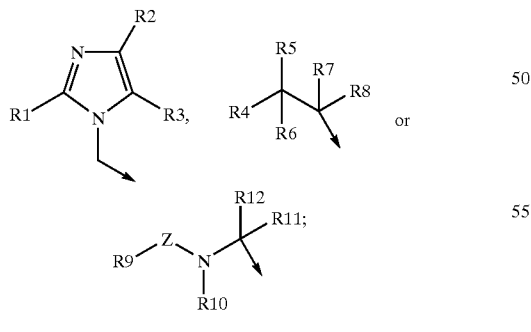

R(1) is hydrogen, alkyl having 1, 2, 3 or 4 carbon atoms or phenyl, which is unsubstituted or substituted by a radical from F, Cl, CF$_3$, methyl, methoxy or hydroxyl; or
R(1) is heteroaryl having 1, 2, 3, 4, 5, 6, 7, 8 and 9 carbon atoms, which is unsubstituted or substituted by a radical from F, Cl, CF$_3$, CH$_3$, methoxy or hydroxyl; or R(1) is cycloalkyl having 3, 4, 5, 6 or 7 carbon atoms;
R(2) and R(3) independently of one another are hydrogen, F, Cl, CF$_3$, —CN, —NO$_2$, CO—R(24) or O—R(25),
   R(24) is hydrogen, alkyl having 1, 2, 3 or 4 carbon atoms, OR(26) or phenyl, which is unsubstituted or substituted by a substituent from F, Cl, CF$_3$, methyl, methoxy or hydroxyl,
   R(26) is hydrogen or alkyl having 1, 2, 3 or 4 carbon atoms,
   R(25) is hydrogen, alkyl having 1, 2, 3 or 4 carbon atoms, or phenyl, which is unsubstituted or substituted by a substituent from F, Cl, CF$_3$, methyl, methoxy or hydroxyl, or
R(2) and R(3) independently of one another are alkyl having 1, 2, 3 or 4 carbon atoms, cycloalkyl having 3, 4, 5, 6 or 7 carbon atoms or phenyl, which is unsubstituted or substituted by a substituent from F, Cl, CF$_3$, methyl, methoxy or hydroxyl; or
R(2) and R(3) independently of one another are heteroaryl having 1, 2, 3, 4, 5, 6, 7, 8 or 9 carbon atoms, which is unsubstituted or substituted by 1, 2 or 3 identical or different radicals from F, Cl, CF$_3$, CH$_3$, methoxy or hydroxyl; or
R(2) and R(3) independently of one another are
   —SO$_f$—R(37),
   R(37) is alkyl having 1, 2, 3 or 4 carbon atoms, cycloalkyl having 3, 4, 5, 6 or 7 carbon atoms or phenyl, which is unsubstituted or substituted by a radical from F, Cl, CF$_3$, methyl, methoxy or hydroxyl;
   f is zero or 2;
R(4) is methyl, ethyl, 1-naphthyl, 2-naphthyl, cycloalkyl having 3, 4, 5, 6 or 7 carbon atoms or —C$_i$H$_{2i}$-phenyl, i is zero or 1; or
R(4) and R(6) together with the carbon atom carrying them are cycloalkyl having 3, 4, 5, 6 or 7 carbon atoms or fluorenyl;
R(5) and R(7) independently of one another are hydrogen or fluorine; or together are a second bond between the carbon atoms carrying the radicals R(6) and R(8);
R(6) and R(8) independently of one another are hydrogen, F, CF$_3$, O—R(56), alkyl having 1, 2, 3 or 4 carbon atoms, —C$_k$H$_{2k}$-phenyl, where the phenyl moiety is unsubstituted or substituted by 1, 2 or 3 identical or different radicals from F, Cl, CF$_3$, methyl, methoxy or hydroxyl;
k is zero or 1
R(56) is hydrogen, alkyl having 1, 2, 3 or 4 carbon atoms, or phenyl, which is unsubstituted or substituted by 1, 2 or 3 identical or different radicals from F, Cl, CF$_3$, methyl, methoxy or hydroxyl, or
R(56) is heteroaryl having 1, 2, 3, 4, 5, 6, 7, 8 or 9 carbon atoms, which is unsubstituted or substituted by 1, 2 or 3 identical or different radicals from F, Cl, CF$_3$, CH$_3$, methoxy or hydroxyl;
R(9)
   is alkyl having 1, 2, 3 or 4 carbon atoms;
   alkenyl having 2, 3 or 4 carbon atoms; or —C$_I$H$_{2I-II}$—A;
   II is zero or 2; and
   I is zero 1, 2 or 3;
      where I is unequal to zero or 1, when II is equal to 2;

R(10) is hydrogen;
alkyl having 1, 2, 3 or 4 carbon atoms;
alkenyl having 2, 3 or 4 carbon atoms; or —$C_mH_{2m-mm}$—B, mm is zero or 2; and
m is zero, 1, 2 or 3;
where m is unequal to zero or 1, when mm is equal to 2;

R(11) and R(12) independently of one another are hydrogen or methyl;
Z is carbonyl or sulfonyl;
A and B independently of one another are
1. phenyl;
2. a radical as defined in 1, substituted by 1, 2 or 3 identical or different radicals from alkyl having 1, 2, 3 or 4 carbon atoms, F, Cl, $CF_3$, $SO_2R(63)$, $OR(64)$, —CN or CO—R(67);
3. 1-naphthyl or 2-naphthyl;
4. a radical as defined in 3, substituted by a radical from alkyl having 1, 2, 3 or 4 carbon atoms, F, Cl, $CF_3$, $CH_3$, methoxy or hydroxyl;
5. heteroaryl having 1, 2, 3, 4, 5, 6, 7, 8 or 9 carbon atoms;
6. a radical as defined in 5, substituted by a radical from F, Cl, $CF_3$, $CH_3$, methoxy or hydroxyl; or
7. cycloalkyl having 3, 4, 5, 6 or 7 carbon atoms;
R(63) is alkyl having 1, 2, 3 or 4 carbon atoms;
R(67) is alkyl having 1, 2, 3 or 4 carbon atoms or O-alkyl having 1, 2, 3 or 4 carbon atoms;
R(64) is hydrogen or alkyl having 1, 2, 3 or 4 carbon atoms;
R(13), R(14) and R(15) independently of one another are hydrogen, alkyl having 1, 2, 3 or 4 carbon atoms, F, Cl, $CF_3$, —CN, $SO_q$—R(79), CO—R(80) or O—R(81);
q is zero or 2,
R(79) is alkyl having 1, 2, 3 or 4 carbon atoms or phenyl, which is unsubstituted or substituted by 1, 2 or 3 identical or different radicals from F, Cl, $CF_3$, methyl, methoxy or hydroxyl;
R(80) is hydrogen, alkyl having 1, 2, 3 or 4 carbon atoms or OR(84);
R(84) is hydrogen or alkyl having 1, 2, 3 or 4 carbon atoms;
R(81) is hydrogen, alkyl having 1, 2, 3 or 4 carbon atoms or phenyl, which is unsubstituted or substituted by 1, 2 or 3 identical or different radicals from F, Cl, $CF_3$, methyl, methoxy or hydroxyl;
Y is CR(16)R(17), CO, S, $SO_2$, O, or NR(18);
R(16) is hydrogen or —OR(85),
R(85) is hydrogen or alkyl having 1, 2, 3 or 4 carbon atoms or COR(86);
R(86) is alkyl having 1, 2, 3 or 4 carbon atoms or phenyl, which is unsubstituted or substituted by a radical from F, Cl, $CF_3$, methyl or methoxy;
R(17) is hydrogen or alkyl having 1, 2, 3 or 4 carbon atoms;
R(18) is hydrogen or alkyl having 1, 2, 3 or 4 carbon atoms, COR(87) or $SO_2R(88)$,
R(87), R(88) independently of one another are alkyl having 1, 2, 3 or 4 carbon atoms, cycloalkyl having 3, 4, 5 or 6 carbon atoms or phenyl, which is unsubstituted or substituted by a radical from F, Cl, Br, I, $CF_3$, methyl or methoxy.

4. A compound as claimed in claim 1, in which:
X is

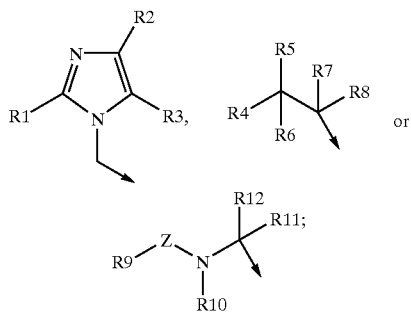

R(1) is alkyl having 1, 2, 3 or 4 carbon atoms or phenyl, which is unsubstituted or substituted by a radical from F, Cl, $CF_3$, methyl or methoxy; or
R(1) is heteroaryl having 1, 2, 3, 4, 5, 6, 7, 8 or 9 carbon atoms, which is unsubstituted or substituted by a radical from F, Cl, $CF_3$, $CH_3$ or methoxy; or
R(1) is cycloalkyl having 3, 4, 5, 6 or 7 carbon atoms;
R(2) and R(3) independently of one another are hydrogen, F, Cl, $CF_3$, —CN, CO—R(24) or O—R(25);
R(24) is hydrogen, alkyl having 1, 2, 3 or 4 carbon atoms, OR(26) or phenyl, which is unsubstituted or substituted by a radical from F, Cl, $CF_3$, methyl or methoxy;
R(26) is hydrogen, methyl or ethyl;
R(25) is hydrogen, alkyl having 1, 2, 3 or 4 carbon atoms, or phenyl, which is unsubstituted or substituted by a radical from F, Cl, $CF_3$, methyl or methoxy; or
R(25) is heteroaryl having 1, 2, 3, 4, 5, 6, 7, 8 or 9 carbon atoms, which is unsubstituted or substituted by a radical from F, Cl, $CF_3$, $CH_3$ or methoxy; or
R(2) and R(3) independently of one another are alkyl having 1, 2, 3 or 4 carbon atoms, cycloalkyl having 3, 4, 5, 6 or 7 carbon atoms, or phenyl, which is unsubstituted or substituted by a radical from F, Cl, $CF_3$, methyl or methoxy; or
R(2) and R(3) independently of one another are heteroaryl having 1, 2, 3, 4, 5, 6, 7, 8 or 9 carbon atoms, which is unsubstituted or substituted by a radical from F, Cl, $CF_3$, $CH_3$ or methoxy; or
R(2) and R(3) independently of one another are —$SO_f$—R(37);
R(37) is alkyl having 1, 2, 3 or 4 carbon atoms or phenyl, which is unsubstituted or substituted by a radical from F, Cl, $CF_3$, methyl or methoxy;
f is zero or 2;
R(4) is methyl, ethyl, 1-naphthyl, 2-naphthyl, cycloalkyl having 3, 4, 5, 6 or 7 carbon atoms or phenyl;
R(4) and R(6) together with the carbon atom carrying them are cycloalkyl having 3, 4, 5 or 6 carbon atoms or fluorenyl;
R(5) and R(7) independently of one another are hydrogen or together are a second bond between the carbon atoms carrying the radicals R(6) and R(8);
R(6) and R(8) independently of one another are hydrogen, $CF_3$, O—R(56), alkyl having 1, 2, 3 or 4 carbon atoms or phenyl, where phenyl is unsubstituted or substituted by a radical from F, Cl, $CF_3$, methyl or methoxy;
R(56) is hydrogen, alkyl having 1, 2, 3 or 4 carbon atoms, or phenyl, which is unsubstituted or substituted by a radical from F, Cl, $CF_3$, methyl or methoxy; or R(56) is heteroaryl having 1 2, 3, 4, 4, 6, 7, 8 or 9 carbon atoms, which is unsubstituted or substituted by a radical from F, Cl, CF$_3$, CH$_3$ or methoxy;

R(9)
is alkyl having 1, 2, 3 or 4 carbon atoms;
alkenyl having 2, 3 or 4 carbon atoms; or —C$_I$H$_{2I-II}$—A,
II is zero or 2; and
I is zero, 1, 2 or 3;
where I is unequal to zero or 1, when II is equal to 2;

R(10) is hydrogen;
alkyl having 1, 2, 3 or 4 carbon atoms;
alkenyl having 2, 3 or 4 carbon atoms; or —C$_m$H$_{2m-mm}$—B,
mm is zero or 2; and
m is zero, 1, 2 or 3;
where m is unequal to zero or 1, when mm is equal to 2;

R(11) and R(12) independently of one another are hydrogen or methyl;

Z is carbonyl or sulfonyl;

A and B independently of one another are
1. phenyl;
2. a radical as defined in 1, substituted by a radical from alkyl having 1, 2, 3 or 4 carbon atoms, F, Cl, CF$_3$, SO$_2$R(63), OR(64), —CN, or CO—R(67);
3. 1-naphthyl or 2-naphthyl;
4. a radical as defined in 3, substituted by a radical from alkyl having 1, 2, 3 or 4 carbon atoms, F, Cl, CF$_3$, CH$_3$ or methoxy;
5. heteroaryl having 1, 2, 3, 4, 5, 6, 7, 8 or 9 carbon atoms;
6. a radical as defined in 5, substituted by a radical from F, Cl, CF$_3$, CH$_3$ or methoxy; or
7. cycloalkyl having 3, 4, 5, 6 or 7 carbon atoms;
R(63) is alkyl having 1, 2, 3 or 4 carbon atoms;
R(64) is hydrogen or alkyl having 1, 2, 3 or 4 carbon atoms;
R(67) is alkyl having 1, 2, 3 or 4 carbon atoms or O-alkyl having 1, 2, 3 or 4 carbon atoms;

R(13), R(14) and R(15) independently of one another are hydrogen, methyl, F, Cl, CF$_3$, —CN, SO$_2$—R(79), CO—R(80) or O—R (81);
R(79) is alkyl having 1, 2, 3 or 4 carbon atoms or phenyl, which is unsubstituted or substituted by a radical from F, Cl, CF$_3$, methyl or methoxy;
R(80) is hydrogen, methyl or —OR(84);
R(84) is hydrogen or alkyl having 1, 2, 3 or 4 carbon atoms;
R(81) is hydrogen, alkyl having 1, 2, 3 or 4 carbon atoms or phenyl, which is unsubstituted or substituted by a radical from F, Cl, CF$_3$, methyl or methoxy;

Y is CR(16)R(17), CO, S or SO$_2$;
R(16) is hydrogen or —OR(85);
R(85) is hydrogen, methyl or COR(86)
R(86) is methyl, cyclopentyl, cyclohexyl or phenyl, which is unsubstituted or substituted by a radical from F, Cl, CF$_3$, methyl or methoxy;
R(17) is hydrogen or methyl.

5. A compound as claimed in claim 1, in which:
X is

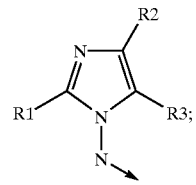

R(1) is alkyl having 1, 2, 3 or 4 carbon atoms or phenyl, which is unsubstituted or substituted by a radical from F, Cl, CF$_3$, methyl or methoxy;
R(2) and R(3) independently of one another are hydrogen, F, Cl, CF$_3$, —CN, CO—R(24) or O—R(25),
R(24) is hydrogen, alkyl having 1, 2, 3 or 4 carbon atoms, OR(26) or phenyl, which is unsubstituted or substituted by a radical from F, Cl, CF$_3$, methyl or methoxy;
R(26) is hydrogen, methyl or ethyl;
R(25) is hydrogen, alkyl having 1, 2, 3 or 4 carbon atoms, or phenyl, which is unsubstituted or substituted by a radical from F, Cl, CF$_3$, methyl or methoxy; or
R(25) is heteroaryl having 1, 2, 3, 4, 5, 6, 7, 8 or 9 carbon atoms, which is unsubstituted or substituted by a radical from F, Cl, CF$_3$, CH$_3$ or methoxy;
R(2) and R(3) independently of one another are alkyl having 1, 2, 3 or 4 carbon atoms, or cycloalkyl having 3, 4, 5, 6 or 7 carbon atoms; or
R(2) and R(3) independently of one another are phenyl, which is unsubstituted or substituted by a radical from F, Cl, CF$_3$, methyl or methoxy; or
R(2) and R(3) independently of one another are heteroaryl having 1, 2, 3, 4, 5, 6, 7, 8 or 9 carbon atoms, which is unsubstituted or substituted by a radical from F, Cl, CF$_3$, CH$_3$ or methoxy; or
R(2) and R(3) independently of one another are
—SO$_f$—R(37),
R(37) is alkyl having 1, 2, 3 or 4 carbon atoms or phenyl, which is unsubstituted or substituted by a radical from F, Cl, CF$_3$, methyl or methoxy;
f is zero or 2;

R(13), R(14) and R(15) independently of one another are hydrogen, methyl, F, Cl, CF$_3$, —CN, SO$_2$—R(79), CO—R(80) or O—R(81);
R(79) and R(81) independently of one another are alkyl having 1, 2, 3 or 4 carbon atoms or phenyl, which is unsubstituted or substituted by a radical from F, Cl, CF$_3$, methyl or methoxy;
R(80) is hydrogen, methyl or OR(84);
R(84) is hydrogen or alkyl having 1, 2, 3 or 4 carbon atoms;
Y is methylene.

6. A pharmaceutical composition comprising an effective amount of at least one compound of claim 1 and a pharmaceutically acceptable carrier.

7. A pharmaceutical composition as claimed in claim 6, further comprising an effective amount of at least one of
(A) one or more NHE inhibitors or a physiologically tolerable salt thereof; and
(B) one or more compounds of another cardiovascular class of active molecules or a physiologically tolerable salt thereof.

8. A method of inhibiting the sodium-dependent bicarbonate/chloride exchanger (NCBE), comprising administering an effective amount of at least one compound of claim 1 to a host in need of said inhibition.

9. A method of treating cardiac infarct, angina pectoris, one or more illnesses caused by ischemic conditions, impaired respiratory drive, one or more ischemic conditions of the heart, one or more ischemic conditions of the peripheral and central nervous system, stroke, one or more ischemic conditions of peripheral organs and limbs, one or more illnesses in which cell proliferation is a primary or secondary cause, or one or more states of shock, comprising administering an effective amount of at least one compound of claim 1 to a host in need of said treatment.

10. A method of treating one or more carcinomatous disorders, comprising administering an effective amount of at least one compound of claim 1 to a host in need of said treatment.

11. A method of treating cardiac infarct, angina pectoris, one or more illnesses caused by ischemic conditions, impaired respiratory drive, one or more ischemic conditions of the heart, one or more ischemic conditions of the peripheral and central nervous system, stroke, one or more ischemic conditions of peripheral organs and limbs, one or more illnesses in which cell proliferation is a primary or secondary cause, or one or more states of shock, comprising administering a pharmaceutical composition as claimed in claim 6 to a host in need of said treatment.

12. A method of treating one or more carcinomatous disorders, comprising administering a pharmaceutical composition as claimed in claim 7 to a host in need of said treatment.

13. A pharmaceutical composition comprising an effective amount of at least one compound of claim 5 and a pharmaceutically acceptable carrier.

14. A method of treating cardiac infarct, angina pectoris, one or more illnesses caused by ischemic conditions, impaired respiratory drive, one or more ischemic conditions of the heart, one or more ischemic conditions of the peripheral and central nervous system, stroke, one or more ischemic conditions of peripheral organs and limbs, one or more illnesses in which cell proliferation is a primary or secondary cause, or one or more states of shock, comprising administering a pharmaceutical composition as claimed in claim 7 to a host in need of said treatment.

15. A method of treating one or more carcinomatous disorders, comprising administering a pharmaceutical composition as claimed in claim 7 to a host in need of said treatment.

16. A process for preparing a compound as claimed in claim 1, which comprises reacting a compound of the formula (II)

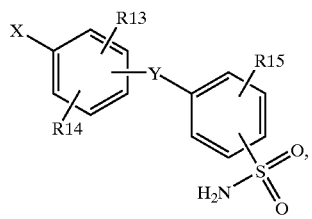

II wherein X, Y, R(13), R(14), and R(15) are as defined in claim 1, with cyanogen bromide in a dipolar aprotic solvent which is stable to cyanogen bromide using a strong auxiliary base.

17. A process as claimed in claim 16, wherein the reaction step occurs at a temperature ranging from 0° C. to the boiling point of the solvent used, inclusive.

18. A process as claimed in claim 16, wherein the reaction step occurs at a temperature ranging from 60° C. to 120° C., inclusive.

19. A process as claimed in claim 16, wherein the solvent is acetonitrile, DMA, TMU, or NMP.

20. A process as claimed in claim 16, wherein the base is $K_2CO_3$ or $Cs_2CO_3$.

21. The method as claimed in claim 9, wherein the host is given one or more doses ranging from 0.001 to 10 mg, inclusive, of at least one compound as claimed in claim 1 per kg of the host's body weight.

22. The method as claimed in claim 9, wherein the host is given one or more doses ranging from 0.01 to 1 mg, inclusive, of at least one compound as claimed in claim 1 perkg of the host's body weight.

23. The method as claimed in claim 9, wherein the host is given one or more doses ranging from 10 to 200 mg, inclusive, of at least one compound as claimed in claim 1 per kg of the host's body weight.

24. A method of preserving or storing an organ, comprising treating said organ with an effective amount of at least one compound of claim 1.

25. A method of preserving or storing an organ, comprising treating said organ with a pharmaceutical composition as claimed in claim 6.

26. A method of preserving or storing an organ, comprising treating said organ with a pharmaceutical composition as claimed in claim 7.

27. A method of treating a host susceptible to developing or redeveloping cardiac infarct, angina pectoris, one or more illnesses caused by ischemic conditions, impaired respiratory drive, one or more ischemic conditions of the heart, one or more ischemic conditions of the peripheral and central nervous system, stroke, one or more ischemic conditions of peripheral organs and limbs, one or more illnesses in which cell proliferation is a primary or secondary cause, or one or more states of shock, comprising administering an effective amount of at least one compound of claim 1 to said host.

28. A method of treating a host susceptible to developing or redeveloping cardiac infarct, angina pectoris, one or more illnesses caused by ischemic conditions, impaired respiratory drive, one or more ischemic conditions of the heart, one or more ischemic conditions of the peripheral and central nervous system, stroke, one or more ischemic conditions of peripheral organs and limbs, one or more illnesses in which cell proliferation is a primary or secondary cause, or one or more states of shock, comprising administering an effective amount of at least one compound of claim 6 to said host.

29. A method of treating a host susceptible to developing or redeveloping cardiac infarct, angina pectoris, one or more illnesses caused by ischemic conditions, impaired respiratory drive, one or more ischemic conditions of the heart, one or more iscllemic conditions of the peripheral and central nervous system, stroke, one or more ischemic conditions of peripheral organs and limbs, one or more illnesses in which cell proliferation is a primary or secondary cause, or one or more states of shock, comprising administering an effective amount of at least one compound of claim 7 to said host.

30. A compound as claimed in claim 1, in which A and B independently of one another are phenyl, 1-naphthyl or 2-naphthyl.

* * * * *

UNITED STATES PATENT AND TRADEMARK OFFICE
CERTIFICATE OF CORRECTION

PATENT NO. : 6,573,288 B1
DATED : June 3, 2003
INVENTOR(S) : Andreas Weichert et al.

It is certified that error appears in the above-identified patent and that said Letters Patent is hereby corrected as shown below:

Column 32,
Line 53, after "4 carbon atoms,", insert -- or --.
Line 66, "-$C_IH_{2I-II}$-A;" should read -- -$C_1H_{21-ll}$-A; --.
Line 67, "II is zero" should read -- ll is zero --.

Column 33,
Line 1, "I is zero," should read -- 1 is zero, --.
Line 2, "I is unequal" should read -- 1 is unequal --; and "II is equal" should read -- ll is equal --.
Line 10, "1,2,3 or 4;" should read -- 1, 2, 3 or 4; --.

Column 36,
Line 17, "-$C_IH_{2I-II}$-A;" should read -- -$C_1H_{21-ll}$-A; --.
Line 18, "II is zero" should read -- ll is zero --.
Line 19, "I is zero," should read -- 1 is zero, --.
Line 20, "I is unequal" should read -- 1 is unequal --; and "II is equal" should read -- ll is equal --.
Line 48, "having 1 2," should read -- having 1, 2, --.
Line 60, "1,2 or 3;" should read -- 1, 2 or 3; --.

Column 38,
Line 63, "-$C_IH_{2I-II}$-A;" should read -- -$C_1H_{21-ll}$-A; --.
Line 64, "II is zero" should read -- ll is zero --.
Line 65, "I is zero" should read -- 1 is zero --.
Line 66, "I is unequal" should read -- 1 is unequal --; and "II is equal" should read -- ll is equal --.

Column 41,
Line 1, "4, 4, 6," should read -- 4, 5, 6, --.
Line 9, "-$C_IH_{2I-II}$-A," should read -- -$C_1H_{21-ll}$-A, --.
Line 10, "II is zero" should read -- ll is zero --.
Line 11, "I is zero," should read -- 1 is zero, --.
Line 12, "I is unequal" should read -- 1 is unequal --; and "II is equal" should read -- ll is equal --.

UNITED STATES PATENT AND TRADEMARK OFFICE
CERTIFICATE OF CORRECTION

PATENT NO. : 6,573,288 B1
DATED : June 3, 2003
INVENTOR(S) : Andreas Weichert et al.

It is certified that error appears in the above-identified patent and that said Letters Patent is hereby corrected as shown below:

Column 42,
Between lines 3-10, in the struture

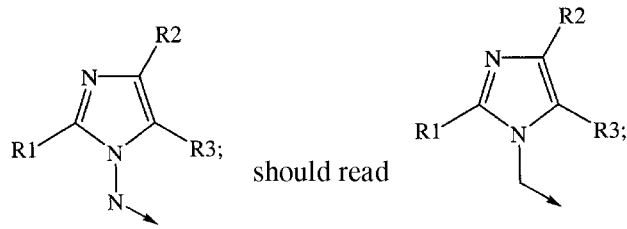 should read

Line 29, after "$CH_3$ or methoxy;", insert -- or --.

Column 43,
Line 31, "claim 7" should read -- claim 6 --.

Column 44,
Line 18, "perkg" should read -- per kg --.
Line 57, "iscllemic" should read -- ischemic --.

Signed and Sealed this

Sixteenth Day of August, 2005

JON W. DUDAS
*Director of the United States Patent and Trademark Office*